(12) United States Patent
Flohr et al.

(10) Patent No.: US 7,122,545 B2
(45) Date of Patent: Oct. 17, 2006

(54) IMIDAZO-BENZOTHIAZOLES

(75) Inventors: Alexander Flohr, Basel (CH); Roland Jakob-Roetne, Inzlingen (DE); Roger David Norcross, Rheinfelden (CH); Claus Riemer, Freiburg (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 80 days.

(21) Appl. No.: 10/843,241

(22) Filed: May 11, 2004

(65) Prior Publication Data

US 2004/0229862 A1 Nov. 18, 2004

(30) Foreign Application Priority Data

May 13, 2003 (EP) ................... 03009842

(51) Int. Cl.
*A61K 31/5377* (2006.01)
*A61K 31/55* (2006.01)
*A61K 31/428* (2006.01)
*C07D 413/02* (2006.01)
*C07D 487/04* (2006.01)
*C07D 417/04* (2006.01)

(52) U.S. Cl. ................. 514/235.8; 514/215; 514/367; 544/127; 544/135; 540/578; 548/159

(58) Field of Classification Search ............ None
See application file for complete search history.

(56) References Cited

U.S. PATENT DOCUMENTS 5,378,844 A * 1/1995 Brufani et al. .............. 544/272
6,037,473 A * 3/2000 Dilk et al. ................. 548/159
6,521,754 B1 * 2/2003 Alanine et al. ............ 544/129
2004/0235842 A1 * 11/2004 Flohr et al. .............. 514/234.2

FOREIGN PATENT DOCUMENTS

EP 1221444 A1 * 7/2002

* cited by examiner

*Primary Examiner*—Kamal A. Saeed
*Assistant Examiner*—Nyeemah Grazier
(74) *Attorney, Agent, or Firm*—George W. Johnston; Patricia S. Rocha-Tramaloni; Kimberly J. Prior

(57) ABSTRACT

The invention relates to 2-imidazo-benzothiazoles of general formula

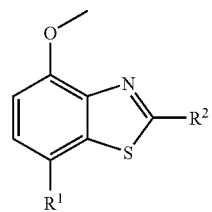

I wherein $R^1$, $R^2$, $R^3$, $R^4$, $R^5$, $R^6$, $R^7$, R', R'', X, R''' and n are defined herein, or a pharmaceutically acceptable salt thereof.

It has been found that the compound of formula I are adenosine receptor ligands with good affinity to the $A_1$ and $A_3$ receptors. These compounds have useful pharmaceutical activities.

20 Claims, No Drawings

IMIDAZO-BENZOTHIAZOLES

FIELD OF THE INVENTION

The invention relates to novel adenosine receptor ligands of formula I

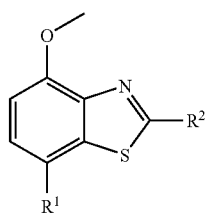

wherein $R^1$ and $R^2$ are described hereinbelow. These ligands (compounds) have a good affinity to the $A_{2A}$ receptors and a high affinity to the $A_1$ and $A_3$ receptors. These compounds are useful, inter alia, in treatment of Alzheimer's disease, depression, Parkinson's disease and ADHD.

BACKGROUND OF THE INVENTION

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzyme A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtypes has been classically characterized by the adenylate cyclase effector system, which utilizes cAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to $G_s$ proteins and activate adenylate cyclase, leading to an increase in cellular cAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326–328 amino acids) was cloned from various species (canine, human, rat, dog, chick, bovine, guinea-pig) with 90–95% sequence identify among the mammalian species. The $A_{2A}$ receptor (409–412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317–320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply: demand within the tissue. The actions of both subtypes are to increase the amount of available oxygen to tissue and to protect cells against damage caused by a short term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is also a neuromodulator, possessing global importance in the modulation of molecular mechanisms underlying many aspects of physiological brain function by mediating central inhibitory effects. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents.

Adenosine antagonists stimulate the activity of the CNS and have proven to be effective as cognition enhancers. Selective $A_{2a}$-antagonists have therapeutic potential in the treatment of various forms of dementia, for example in Alzheimer's disease and are useful as neuroprotective agents. Adenosine $A_{2a}$-receptor antagonists inhibit the release of dopamine from central synaptic terminals and stimulate locomotor activity and consequently improve Parkinsonian symptoms. The central activities of adenosine are also implicated in the molecular mechanism underlying sedation, hypnosis, schizophrenia, anxiety, pain, respiration, depression and substance abuse. Drugs acting at adenosine receptors therefore have therapeutic potential as sedatives, muscle relaxants, antipsychotics, anxiolytics, analgesics, respiratory stimulants and antidepressants, and they may be used in the treatment of ADHD (attention deficit hyperactivity disorder).

An important role for adenosine in the cardiovascular system is as a cardioprotective agent. Levels of endogenous adenosine increase in response to ischaemia and hypoxia, and protect cardiac tissue during and after trauma (preconditioning). Adenosine agonists thus have potential as cardioprotective agents.

Adenosine modulates many aspects of renal function, including renin release, glomerular filtration rate and renal blood flow. Compounds, which antagonize the renal affects of adenosine, have potential as renal protective agents. Furthermore, adenosine $A_3$ and/or $A_{2B}$ antagonists may be useful in the treatment of asthma and other allergic responses or and in the treatment of diabetes mellitus and obesity.

Numerous documents describe the current knowledge on adenosine receptors. These include Bioorganic & Medicinal Chemistry, 6, (1998), 619–641, Bioorganic & Medicinal Chemistry, 6, (1998), 707–719, J. Med. Chem., (1998), 41, 2835–2845, J. Med. Chem., (1998), 41, 3186–3201, J. Med. Chem., (1998), 41, 2126–2133, J. Med. Chem., (1999), 42, 706–721, J. Med. Chem., (1996), 39, 1164–1171, Arch. Pharm. Med. Chem., 332, 39–41, (1999), Am. J. Physiol., 276, H1113–1116, (1999) and Naunyn Schmied, Arch. Pharmacol. 362, 375–381, (2000).

SUMMARY OF THE INVENTION

An aspect of the present invention is directed to the compounds of formula I

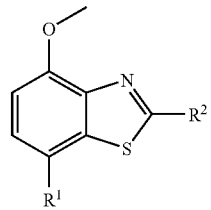

wherein, $R^1$ is selected from the group consisting of phenyl, N-containing heterocycle, O-containing heterocycle and both N- and O-containing heterocycle;

$R^2$ is selected from an imidazol and an annulated imidazol, selected from the group consisting of a)

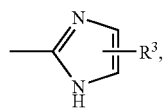

b)

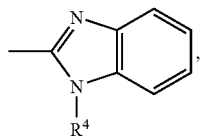

c)

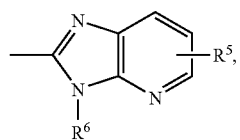

d)

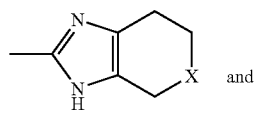

e)

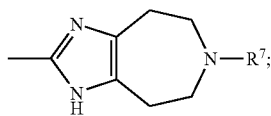

$R^3$ is selected from the group consisting of hydrogen, phenyl, 2,3-dihydro-benzo[1,4]dioxin-6-yl, benzo[b]thiophen-3-yl, 3-methyl-benzo[b]thiophen-2-yl, thiophen-2-yl, thiophen-3-yl and thiophen-2-yl-methyl;

$R^4$ is selected from the group consisting of hydrogen and lower alkyl;

$R^5$ is selected from the group consisting of hydrogen, lower alkyl, halogen, morpholinyl, —NR'R", piperidinyl, piperidinyl substituted by hydroxy, and pyrrol-1-yl;

$R^6$ is selected from the group consisting of hydrogen, benzyl and —$(CH_2)_n$O-lower alkyl;

$R^7$ is selected from the group consisting of hydrogen, —C(O)O-lower alkyl, —C(O)—$C_6H_4$-halogen, —C(O)—$C_6H_4$-lower alkyl, —C(O)-lower alkyl, —C(O)-cycloalkyl, —C(O)—NR'R", —C(O)—$(CH_2)_n$O-lower alkyl, —$S(O)_2$-lower alkyl —$(CH_2)_n$O-lower alkyl, —C(O)-pyridin-4-yl, —C(O)-pyridin-4-yl substituted by lower alkyl, —C(O)-pyridin-4-yl substituted by halogen-lower alkyl, —C(O)-pyridin-4-yl substituted by pyrrol-1-yl-methyl and —$(CH_2)_n$—C(O)—NR'R"; R' and R" are each independently selected from the group consisting of hydrogen, lower alkyl and —$(CH_2)_n$-tetrahydropyran-4-yl;

X is selected from the group consisting of —$CH_2$—, —NR'''— and —O—;

R''' is selected from the group consisting of hydrogen, —C(O)-lower alkyl, —C(O)O-lower alkyl, —C(O)—$C_6H_4CH_3$, and benzyl; and n is 1 or 2;

or a pharmaceutically acceptable salt thereof.

Other embodiments of this invention are directed to methods of manufacture of compounds of formula I, pharmaceutical compositions containing a compound of formula I, and a pharmaceutically acceptable salt thereof, as well as a method of controlling or prevention of illnesses based on the modulation of the adenosine system, such as Alzheimer's disease, Parkinson's disease, Huntington's disease, neuroprotection, schizophrenia, anxiety, pain, respiration deficits, depression, drug addiction, such as amphetamine, cocaine, opioids, ethanol, nicotine, cannabinoids, or against asthma, allergic responses, hypoxia, ischaemia, seizure and substance abuse comprising administering to a patient a therapeutically effective amount of a compound of formula I or a pharmaceutically acceptable salt thereof.

Furthermore, compounds of the present invention are useful as sedatives, muscle relaxants, antipsychotics, antiepileptics, anticonvulsants and cardioprotective agents for disorders such as coronary artery disease and heart failure. Preferred indications in accordance with the present invention are those that depend on the $A_{2A}$ receptor antagonistic activity and which include disorders of the central nervous system, for example the treatment or prevention of Alzheimer's disease, certain depressive disorders, drug addiction, neuroprotection and Parkinson's disease as well as ADHD.

DETAILED DESCRIPTION OF THE INVENTION

As used herein, the term "lower alkyl" refers to a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "cycloalkyl" refers to a saturated carboxylic group, containing 3–7 carbon atoms. A preferred cycloalkyl group is cyclopropyl.

The term "halogen" refers to chlorine, iodine, fluorine and bromine.

The term "lower alkoxy" refers to a group wherein the alkyl residues is as defined above, and which is attached via an oxygen atom.

The term "N and/or O containing heterocycle" refers to a group consisting of morpholinyl, piperidinyl, piperazinyl or tetrahydropyran-2, 3 or 4-yl.

The term "annulated imidazol" refers to a two membered heterocycle, wherein one cycle is the imidazole ring and the annulated group is an aromatic six-membered ring, optionally containing a heteroatom, such as N, or is a non aromatic six or seven membered ring, optionally containing a heteroatom, such as O or N. Preferred are the following annulated imidazoles: benzimidazol-2-yl, 2-imidazo[4,5-b]pyridine, 2-(4,5,6,7-tetrahydrobenzoimidazol-2-yl), 2-(3,4,6,7-tetrahydro-pyrano[3,4-d]imidazole or 4,5,7,8-tetrahydroimidazo[4,5-d]azepin-6-yl.

The term "pharmaceutically acceptable acid addition salts" refers to salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The term "therapeutically effective amount" refers to an amount of at least one compound of formula I, or a pharmaceutically acceptable salt thereof, that modulates adenosine.

In one embodiment, the following compound is encompassed by the present formula I:

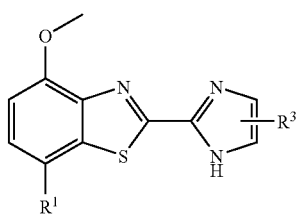

Ia wherein,
$R^1$ is selected from phenyl and a N- and O-containing heterocycle; and
$R^3$ is selected from the group consisting of hydrogen, phenyl, 2,3-dihydro-benzo[1,4]dioxin-6-yl, benzo[b]thiophen-3-yl, 3-methyl-benzo[b]thiophen-2-yl, thiophen-2-yl, thiophen-3-yl and thiophen-2-yl-methyl;
or a pharmaceutically acceptable salt thereof.

In another embodiment, the following compound is encompassed by the present formula I:

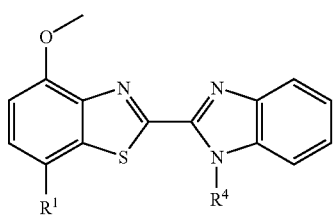

Ib wherein,
$R^1$ is selected from O-containing heterocycle and an N- and O-containing heterocycle; and $R^4$ is selected from hydrogen and lower alkyl;
or a pharmaceutically acceptable salt thereof.

In yet another embodiment, the following compound is encompassed by the present formula I:

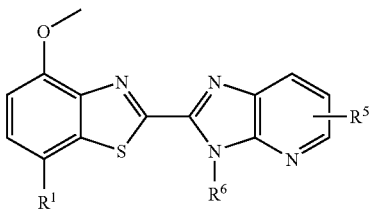

Ic wherein,
$R^1$ is a N- and O-containing heterocycle;
$R^5$ is selected from the group consisting of lower alkyl, halogen, morpholinyl, —NR'R", piperidinyl substituted by hydroxy, and pyrrol-1-yl;
$R^6$ is selected from the group consisting of hydrogen and —$(CH_2)_n$O-lower alkyl; and
R' and R" are each independently selected from the group consisting of lower alkyl and —$(CH_2)_n$-tetrahydropyran-4-yl;
or a pharmaceutically acceptable salt thereof.

In yet another embodiment, the following compound is encompassed by the present formula I:

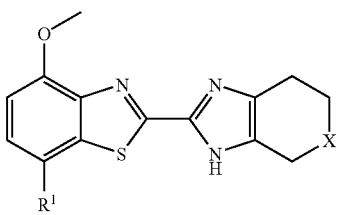

Id wherein,
$R^1$ is a N- and O-containing heterocycle;
X is selected from —NR'''— and —O—;
R''' is hydrogen;
or a pharmaceutically acceptable salt thereof.

In yet another embodiment, the following compound is encompassed by the present formula I:

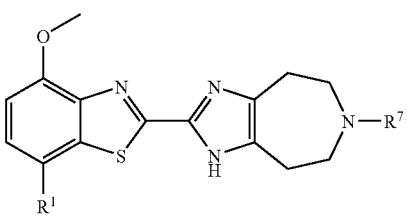

Ie wherein,
$R^1$ is a N- and O-containing heterocycle;
$R^7$ is selected from the group consisting of hydrogen, —C(O)O-lower alkyl, —C(O)—$C_6H_4$-halogen, —C(O)—$C_6H_4$-lower alkyl, —C(O)-lower alkyl, —C(O)-cycloalkyl, —C(O)—NR'R", —C(O)—(CH$_2$)$_n$—O-lower alkyl, —S(O)$_2$-lower alkyl, —(CH$_2$)$_n$O-lower alkyl, —C(O)-pyridin-4-yl substituted by lower alkyl, —C(O)-pyridin-4-yl substituted by halogen-lower alkyl, —C(O)-pyridin-4-yl substituted by pyrrol-1-yl-methyl and —(CH$_2$)$_n$—C(O)—NR'R"; and R' and R" are each independently selected from the group consisting of hydrogen and lower alkyl;

or a pharmaceutically acceptable salt thereof.

Preferred compounds of the present application are compounds of formula I, wherein R$^1$ is morpholinyl.

Further preferred are compounds of formula Ia, for example the following compounds:

2-(1H-imidazol-2-yl)-4-methoxy-7-morpholin-4-yl-benzothiazole,
2-(1H-imidazol-2-yl)-4-methoxy-7-phenyl-benzothiazole,
4-methoxy-7-morpholin-4-yl-2-(4-phenyl-1H-imidazol-2-yl)-benzothiazole,
2-[4-(2,3-dihydro-benzo[1,4]dioxin-6-yl)-1H-imidazol-2-yl]-4-methoxy-7-morpholin-4-yl-benzothiazole,
2-(5-benzo[b]thiophen-3-yl-1H-imidazol-2-yl)-4-methoxy-7-morpholin-4-yl-benzothiazole,
4-methoxy-7-morpholin-4-yl-2-(4-thiophen-2-yl-1H-imidazol-2-yl)-benzothiazole,
4-methoxy-7-morpholin-4-yl-2-(4-thiophen-3-yl-1H-imidazol-2-yl)-benzothiazole and
4-methoxy-7-morpholin-4-yl-2-(4-thiophen-2-ylmethyl-1H-imidazol-2-yl)-benzothiazole.

Preferred are compounds of formula Ib, for example the following compounds:

2-(1H-benzoimidazol-2-yl)-4-methoxy-7-morpholin-4-yl-benzothiazole and
4-methoxy-2-(1-methyl-1H-benzoimidazol-2-yl)-7-morpholin-4-yl-benzothiazole.

Further preferred are compounds of formula Ic, for example the following compounds:

2-(4-methoxy-7-morpholin-4-yl-benzothiazol-2-yl)-5-methyl-3H-imidazo[4,5-b]pyridine,
5-chloro-2-(4-methoxy-7-morpholin-4-yl-benzothiazol-2-yl)-3H-imidazo[4,5-b]pyridine,
5-chloro-3-methoxymethyl-2-(4-methoxy-7-morpholin-4-yl-benzothiazol-2-yl)-3H-imidazo[4,5-b]pyridine,
3-methoxymethyl-2-(4-methoxy-7-morpholin-4-yl-benzothiazol-2-yl)-5-morpholin-4-yl-3H-imidazo[4,5-b]pyridine,
2-(4-methoxy-7-morpholin-4-yl-benzothiazol-2-yl)-5-morpholin-4-yl-3H-imidazo[4,5-b]pyridine,
3-methoxymethyl-2-(4-methoxy-7-morpholin-4-yl-benzothiazol-2-yl)-5-pyrrolidin-1-yl-3H-imidazo[4,5-b]pyridine,
2-(4-methoxy-7-morpholin-4-yl-benzothiazol-2-yl)-5-pyrrolidin-1-yl-3H-imidazo[4,5-b]pyridine,
[2-(4-methoxy-7-morpholin-4-yl-benzothiazol-2-yl)-3H-imidazo[4,5-b]pyridin-5-yl]-dimethyl-amine,
1-[2-(4-methoxy-7-morpholin-4-yl-benzothiazol-2-yl)-3H-imidazo[4,5-b]pyridin-5]-piperidin-4-ol and
[2-(4-methoxy-7-morpholin-4-yl-benzothiazol-2-yl)-3H-imidazo[4,5-b]pyridin-5-yl]-methyl-(tetrahydro-pyran-4-ylmethyl)-amine.

Further preferred are compounds of formula Id, for example the following compounds:

4-methoxy-7-morpholin-4-yl-2-(4,5,6,7-tetrahydro-1H-benzoimidazol-2-yl)-benzothiazole,
2-(4-methoxy-7-morpholin-4-yl-benzothiazol-2-yl)-3,4,6,7-tetrahydro-pyrano[3,4-d]imidazole,
2-(4-methoxy-7-morpholin-4-yl-benzothiazol-2-yl)-3,4,6,7-tetrahydro-imidazo[4,5-c]pyridine-5-carboxylic acid tert-butyl ester,
2-(4-methoxy-7-morpholin-4-yl-benzothiazol-2-yl)-4,5,6,7-tetrahydro-1H-imidazo[4,5-c]pyridine; hydrochloride,
[2-(4-methoxy-7-morpholin-4-yl-benzothiazol-2-yl)-1,4,6,7-tetrahydro-imidazo[4,5-c]pyridin-5-yl]-o-tolyl-methanone,
1-[2-(4-methoxy-7-morpholin-4-yl-benzothiazol-2-yl)-1,4,6,7-tetrahydro-imidazo[4,5-c]pyridin-5-yl]-ethanone and
2-(4-methoxy-7-morpholin-4-yl-benzothiazol-2-yl)-1,4,6,7-tetrahydro-imidazo[4,5-c]pyridine-5-carboxylic acid ethyl ester.

Further preferred are compounds of formula Ie, for example the following compounds:

2-(4-methoxy-7-morpholin-4-yl-benzothiazol-2-yl)-4,5,7,8-tetrahydro-1H-imidazo[4,5-d]azepine-6-carboxylic acid tert-butyl ester,
2-(4-methoxy-7-morpholin-4-yl-benzothiazol-2-yl)-1,4,5,6,7,8-hexahydro-imidazo[4,5-d]azepine hydrochloride,
(4-fluoro-phenyl)-[2-(4-methoxy-7-morpholin-4-yl-benzothiazol-2-yl)-4,5,7,8-tetrahydro-1H-imidazo[4,5-d]azepin-6-yl]-methanone,
1-[2-(4-methoxy-7-morpholin-4-yl-benzothiazol-2-yl)-4,5,7,8-tetrahydro-1H-imidazo[4,5-d]azepin-6-yl]-ethanone,
[2-(4-methoxy-7-morpholin-4-yl-benzothiazol-2-yl)-4,5,7,8-tetrahydro-1H-imidazo[4,5-d]azepin-6-yl]-o-tolyl-methanone,
1-[2-(4-methoxy-7-morpholin-4-yl-benzothiazol-2-yl)-4,5,7,8-tetrahydro-1H-imidazo[4,5-d]azepin-6-yl]-2,2-dimethyl-propan-1-one,
cyclopropyl-[2-(4-methoxy-7-morpholin-4-yl-benzothiazol-2-yl)-4,5,7,8-tetrahydro-1H-imidazo[4,5-d]azepin-6-yl]-methanone,
2-(4-methoxy-7-morpholin-4-yl-benzothiazol-2-yl)-4,5,7,8-tetrahydro-1H-imidazo[4,5-d]azepine-6-carboxylic acid dimethylamide,
2-methoxy-1-[2-(4-methoxy-7-morpholin-4-yl-benzothiazol-2-yl)-4,5,7,8-tetrahydro-1H-imidazo[4,5-d]azepin-6-yl]-ethanone,
2-(4-methoxy-7-morpholin-4-yl-benzothiazol-2-yl)-4,5,7,8-tetrahydro-1H-imidazo[4,5-d]azepine-6-carboxylic acid ethyl ester,
6-methanesulfonyl-2-(4-methoxy-7-morpholin-4-yl-benzothiazol-2-yl)-1,4,5,6,7,8-hexahydro-imidazo[4,5-d]azepine and
6-(2-methoxy-ethyl)-2-(4-methoxy-7-morpholin-4-yl-benzothiazol-2-yl)-1,4,5,6,7,8-hexahydro-imidazo[4,5-d]azepine.

One aspect of the present compounds of formula I and their pharmaceutically acceptable salts can be prepared by methods known in the art, for example, by processes described below, which processes comprise reacting a compound of formula

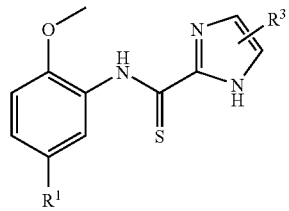

II with K₃FeCN₆/KOH to produce a compound of formula

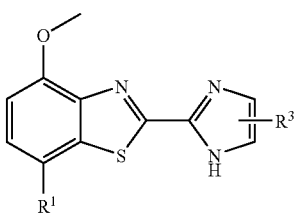

Ia wherein $R^1$ and $R^3$ are as defined above, and if desired, converting the compound obtained into its pharmaceutically acceptable salt.

Another aspect of the present compounds of formula I and their pharmaceutically acceptable salts can be prepared by methods known in the art, for example, by processes described below, which processes comprise cyclizing a compound of formula

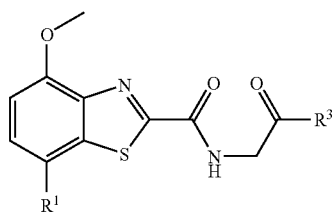

III to produce a compound of formula

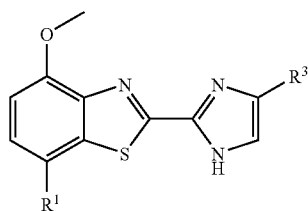

Ia1 wherein $R^1$ and $R^3$ are as described above, and if desired, converting the compound obtained into its pharmaceutically acceptable salt.

Another aspect of the present compounds of formula I and their pharmaceutically acceptable salts can be prepared by methods known in the art, for example, by processes described below, which processes comprise reacting a compound of formula

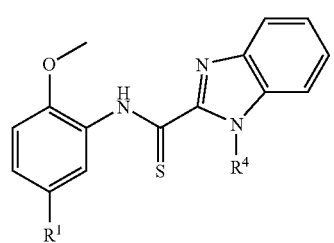

IV with K₃FeCN₆/KOH to produce a compound of formula

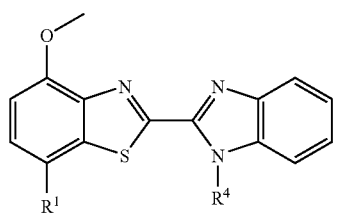

Ib wherein $R^1$ and $R^4$ are as defined above, and if desired, converting the compound obtained into its pharmaceutically acceptable salt.

Another aspect of the present compounds of formula I and their pharmaceutically acceptable salts can be prepared by methods known in the art, for example, by processes described below, which processes comprise methylating a compound of formula

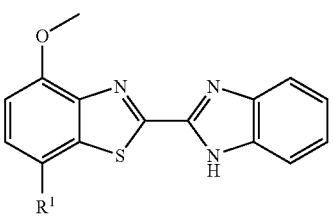

Ib2 to produce a compound of formula

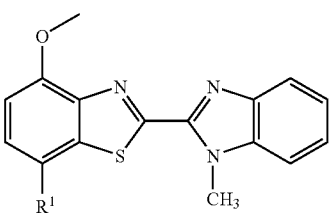

Ib1 wherein $R^1$ is as described above, and if desired, converting the compound obtained into its pharmaceutically acceptable salt.

Another aspect of the present compounds of formula I and their pharmaceutically acceptable salts can be prepared by methods known in the art, for example, by processes described below, which processes comprise reacting a compound of formula

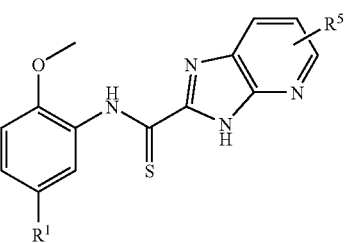

V to produce a compound of formula

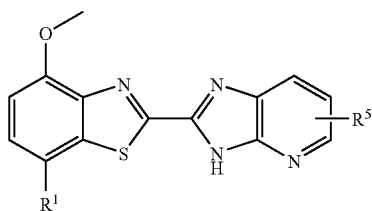

Ic1 wherein R¹ and R⁵ are as described above, and if desired, converting the compound obtained into its pharmaceutically acceptable salt.

Another aspect of the present compounds of formula I and their pharmaceutically acceptable salts can be prepared by methods known in the art, for example, by processes described below, which processes comprise reacting a compound of formula

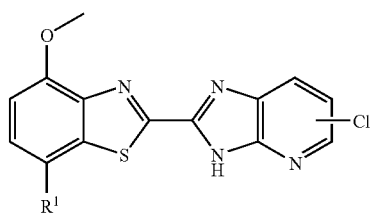

Ic2 with a compound of formula NHR'R" to produce a compound of formula

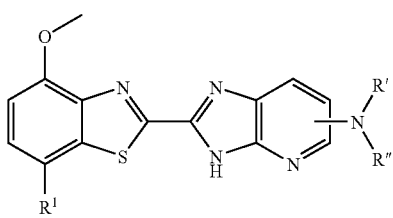

Ic3 wherein R¹ and R'/R" are as described above, and if desired, converting the compound obtained into its pharmaceutically acceptable salt.

Another aspect of the present compounds of formula I and their pharmaceutically acceptable salts can be prepared by methods known in the art, for example, by processes described below, which processes comprise reacting a compound of formula

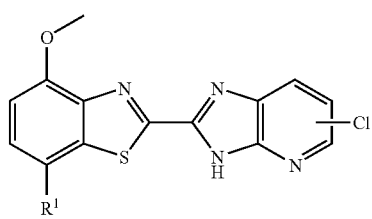

Ic2 with MOMCl/NaH to produce a compound of formula

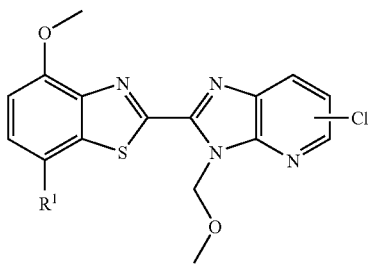

Ic4 wherein R¹ is as described above, and if desired, converting the compound obtained into its pharmaceutically acceptable salt.

Another aspect of the present compounds of formula I and their pharmaceutically acceptable salts can be prepared by methods known in the art, for example, by processes described below, which processes comprise reacting a compound of formula Ic4 with a compound of formula HR⁵ to produce a compound of formula

Ic5 wherein R¹ and R⁵ are as described above, and if desired, converting the compound obtained into its pharmaceutically acceptable salt.

Another aspect of the present compounds of formula I and their pharmaceutically acceptable salts can be prepared by methods known in the art, for example, by processes described below, which processes comprise reacting a compound of formula

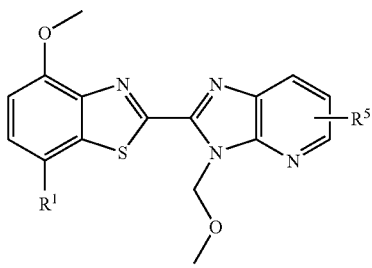

Ic5 with HCl to produce a compound of formula

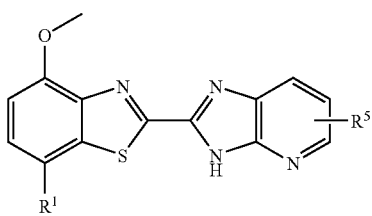

Ic1 wherein $R^1$ and $R^5$ are as described above, and if desired, converting the compound obtained into its pharmaceutically acceptable salt.

Another aspect of the present compounds of formula I and their pharmaceutically acceptable salts can be prepared by methods known in the art, for example, by processes described below, which processes comprise reacting a compound of formula

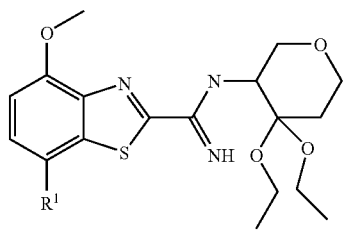

VI with HCl to produce a compound of formula

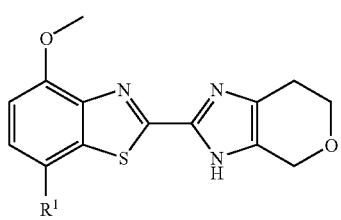

Id1 wherein $R^1$ is as described above, and if desired, converting the compound obtained into its pharmaceutically acceptable salt.

Another aspect of the present compounds of formula I and their pharmaceutically acceptable salts can be prepared by methods known in the art, for example, by processes described below, which processes comprise reacting a compound of formula

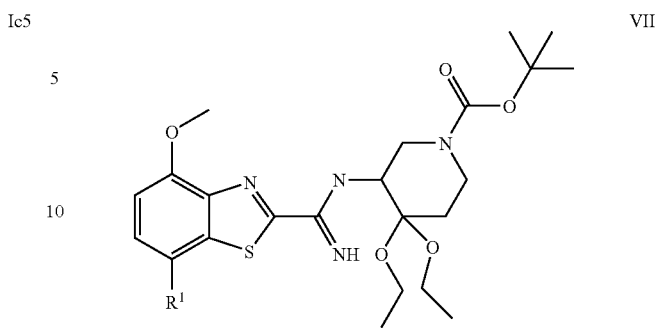

VII with $DMF/BF_3.Et_2O$ to produce a compound of formula

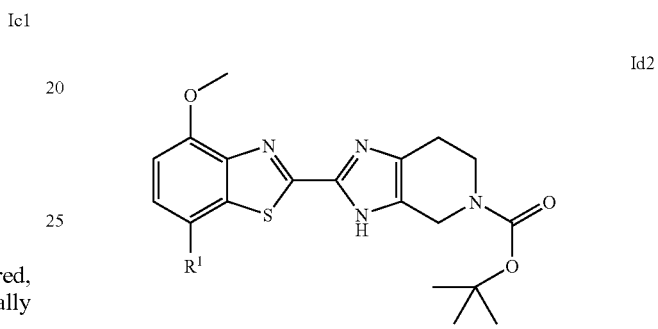

Id2 wherein $R^1$ is as described above, and if desired, converting the compound obtained into its pharmaceutically acceptable salt.

Another aspect of the present compounds of formula I and their pharmaceutically acceptable salts can be prepared by methods known in the art, for example, by processes described below, which processes comprise reacting a compound of formula

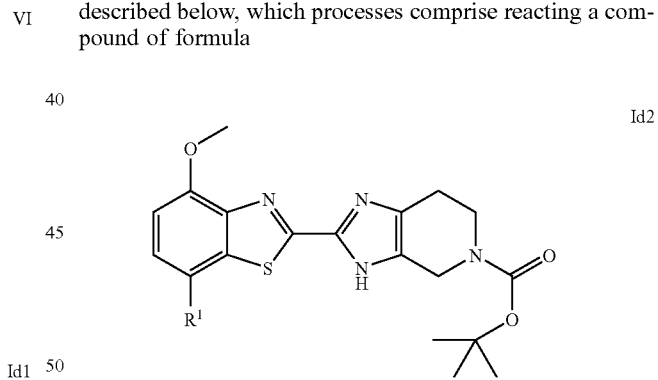

Id2 with HCl to produce a compound of formula

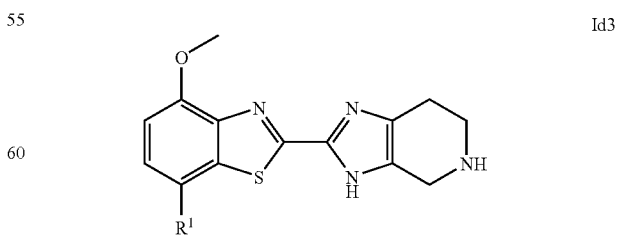

Id3 wherein $R^1$ is as described above, and if desired, converting the compound obtained into its pharmaceutically acceptable salt.

Another aspect of the present compounds of formula I and their pharmaceutically acceptable salts can be prepared by methods known in the art, for example, by processes described below, which processes comprise reacting a compound of formula

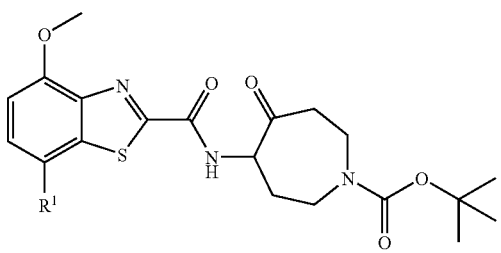

VIII with $CH_3COONH_4$ to produce a compound of formula

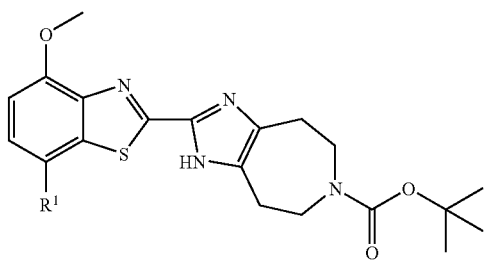

Ie1 wherein $R^1$ is as described above, and if desired, converting the compound obtained into its pharmaceutically acceptable salt.

Another aspect of the present compounds of formula I and their pharmaceutically acceptable salts can be prepared by methods known in the art, for example, by processes described below, which processes comprise reacting a compound of formula

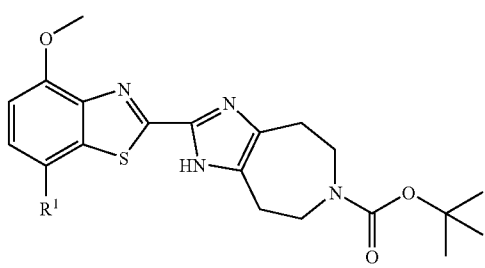

Ie1 with HCl to produce a compound of formula

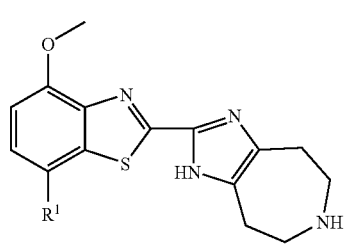

Ie2 wherein $R^1$ is as described above.

The compounds of formula I may be prepared in accordance with process variants a) to n) and with the following schemes 1 to 10. The preparation of 42 specific examples is further described in more detail.

Scheme 1

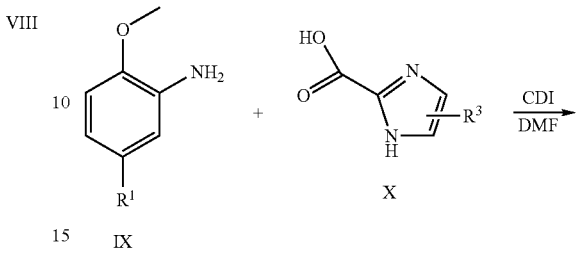

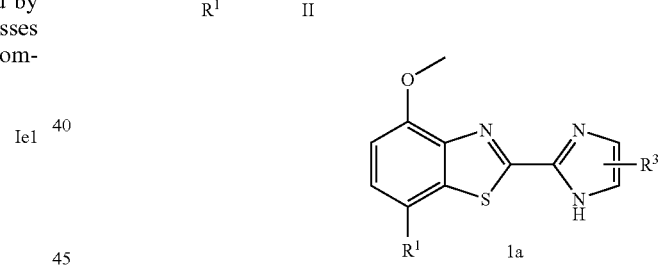

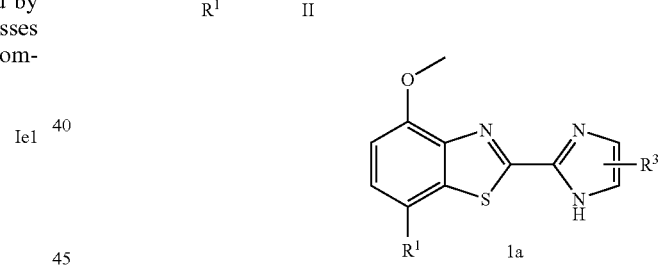

wherein $R^1$ and $R^3$ are described as above and CDI is 1.1'-carbonyl-diimidazole.

According to scheme 1, to a suspension of a imidazole-2-carboxylic acid (X) was added CDI (1,1'-carbonyl-diimidazole) and stirred at ambient temperature for about 1 h. Then the mixture was refluxed and cooled to ambient temperature. 2-Methoxy-5-morpholin-4-yl-phenylamine (for $R^1$=morpholinyl, IX) was added and the reaction mixture was heated to reflux for about 16 h. After workup 1H-imidazole-2-carboxylic acid (2-methoxy-5-morpholin-4-yl-phenyl)-amide (XI) was obtained, which was then treated with the Lawesson reagent. The reaction mixture was then heated to reflux for about 22 h. The obtained 1H-imidazole-2-carbothioic acid (2-methoxy-5-morpholin-4-yl-phenyl)-amide (II) was taken up in water and treated with KOH and potassium hexacyano ferrate to give 2-(1H-imidazol-2-yl)-4-methoxy-7-morpholin-4-yl-benzothiazole (Ia for $R^1$=morpholinyl).

Scheme 2

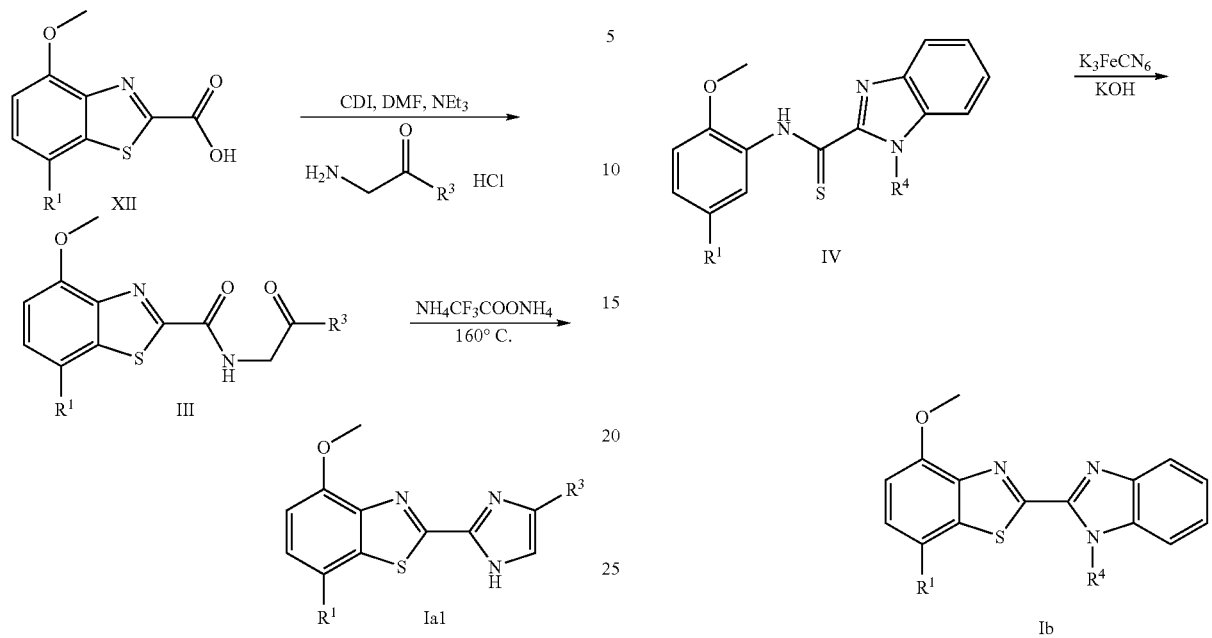

wherein $R^1$ and $R^3$ are as defined above.

In accordance with scheme 2, 4-methoxy-7-morpholin-4-yl-benzothiazole-2-carboxylic acid (for $R^1$=morpholinyl, XII) and CDI (1,1'-carbonyl-diimidazole) was stirred at room temperature for about 1.5 hours. Then, for example, 2-amino-1-(2-thienyl)ethanone hydrochloride (for $R^3$=thienyl) and triethylamine were added and stirring are continued over night at room temperature. Then a mixture of the obtained 4-methoxy-7-morpholin-4-yl-benzothiazole-2-carboxylic acid (2-oxo-2-thiophen-2-yl-ethyl)-amide (III) and ammonium triflouroacetate was melted at about 165° C. for 60 minutes to obtain 4-methoxy-7-morpholin-4-yl-2-(4-thiophen-2-yl-1H-imidazol-2-yl)-benzothiazole (Ia1 for $R^1$=morpholinyl and $R^3$=thienyl).

Scheme 3

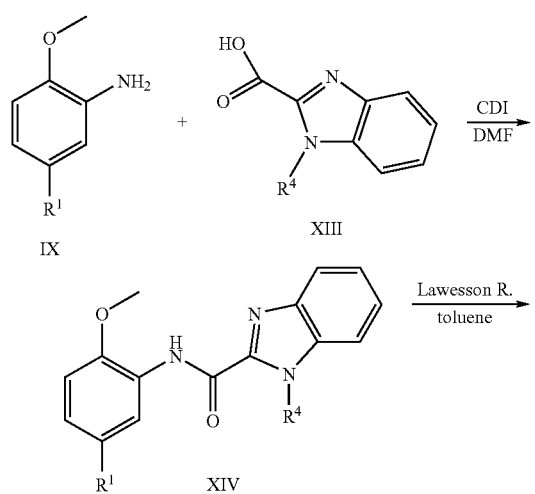

wherein $R^1$ and $R^4$ are as described above.

In accordance with scheme 3, to a suspension of a corresponding benzoimidazole-2-carboxylic acid (XIII) was added CDI and stirred at ambient temperature for about 1 h. Then the mixture is refluxed for about 30 min. After cooling to ambient temperature, 2-methoxy-5-morpholin-4-yl-phenylamine (for $R^1$=morpholinyl, IX) was added and the reaction mixture was heated to reflux for about 16 h. After workup, the corresponding 1H-benzoimidazole-2-carboxylic acid (2-methoxy-5-morpholin-4-yl-phenyl)-amide (XIV) was obtained, which was then taken up in toluene and treated with Lawesson reagent. The reaction mixture was heated to reflux for about 2 h and after workup, the corresponding 1H-benzoimidazole-2-carbothioic acid (2-methoxy-5-morpholin-4-yl-phenyl)-amide (IV) was obtained, which was then taken up in water and treated with KOH and potassium hexacyano ferrate at reflux for about 24 h to obtain the corresponding 2-(1H-benzoimidazol-2-yl)-4-methoxy-7-morpholin-4-yl-benzothiazole (Ib).

Scheme 3a

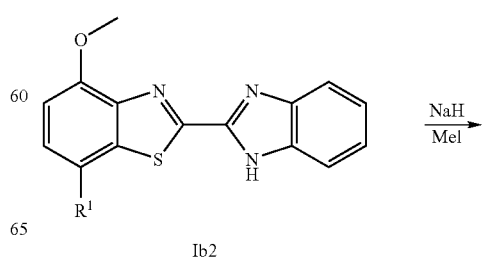

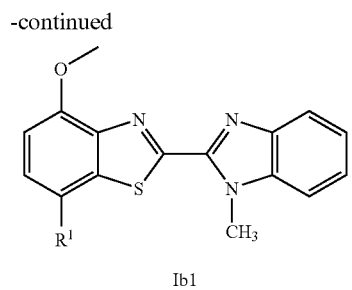

wherein R¹ is as described above.

In case if R³ is hydrogen, a corresponding compound wherein R³ is methyl may be obtained by methylation with MeI in the presence of NaH in conventional manner.

Scheme 4

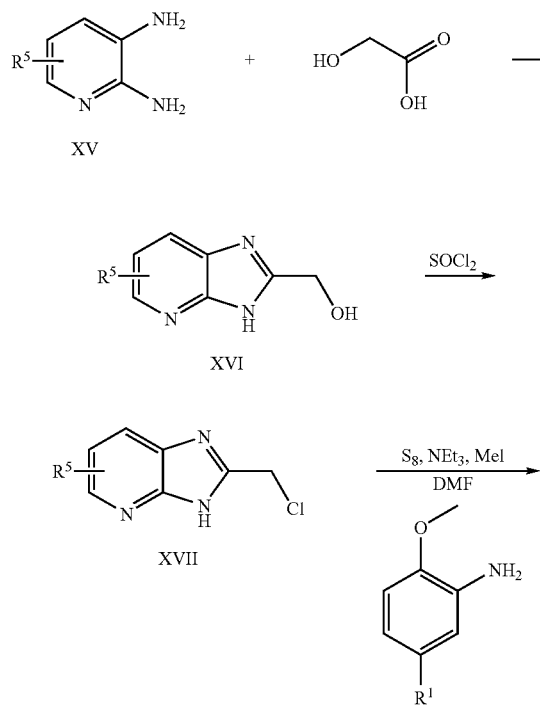

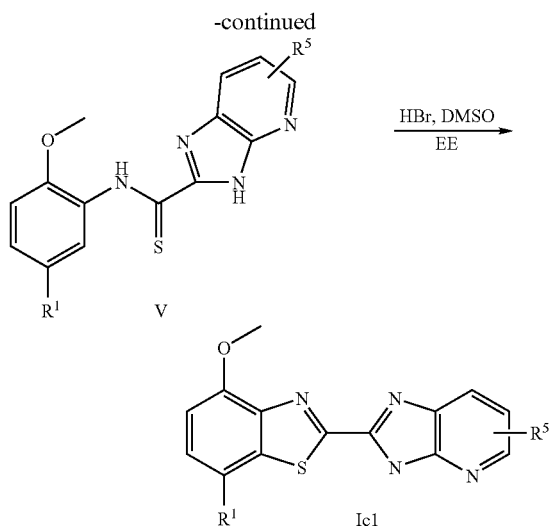

wherein R¹ and R⁵ are as described above.

In accordance with scheme 4, a corresponding 2,3-diamino-6-methyl pyridine (R⁵=methyl, XV) and glycolic acid were heated at 150° C. for about 1 h. The residue was suspended in chloroform and treated with thionyl chloride for about 4 h. After workup 2-chloromethyl-5-methyl-3H-imidazo[4,5-b]pyridine hydrochloride (XVII) was obtained.

Then triethyl amine, sulfur and 2-chloromethyl-5-methyl-3H-imidazo[4,5-b]pyridine hydrochloride were dissolved in DMF and stirred at ambient temperature for about 2 h. After cooling to 0° C., MeI was added and stirring at ambient temperature was continued for 1 h. After workup the obtained product was solved in ethanol and treated with 2-methoxy-5-morpholin-4-yl-phenylamine (for R¹=morpholinyl, for 16 h at reflux. Upon cooling to ambient temperature a precipitate formed, which was isolated and dried in vacuo to obtain the corresponding 5-methyl-3H-imidazo[4,5-b]pyridine-2-carbothioic acid (2-methoxy-5-morpholin-4-yl-phenyl)-amide (V), which was dissolved in ethyl acetate, heated to reflux and treated with HBr in AcOH and DMSO. Stirring at reflux was continued for 2 h. Upon cooling a precipitation formed, which was isolated and worked up to obtain 2-(4-methoxy-7-morpholin-4-yl-benzothiazol-2-yl)-5-methyl-3H-imidazo[4,5-b]pyridine (for R¹=morpholinyl and R⁵=methyl, Ic1).

Scheme 5

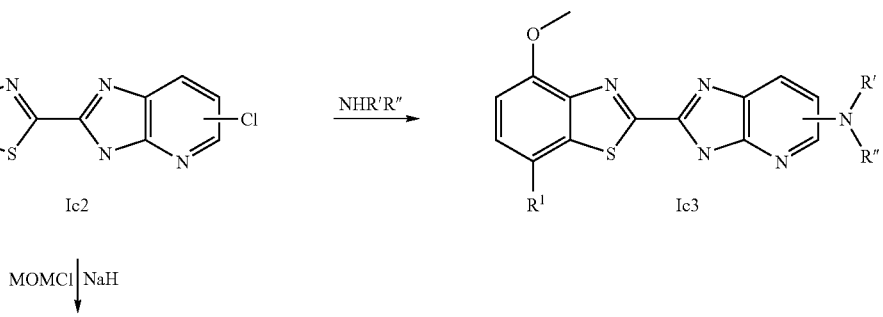

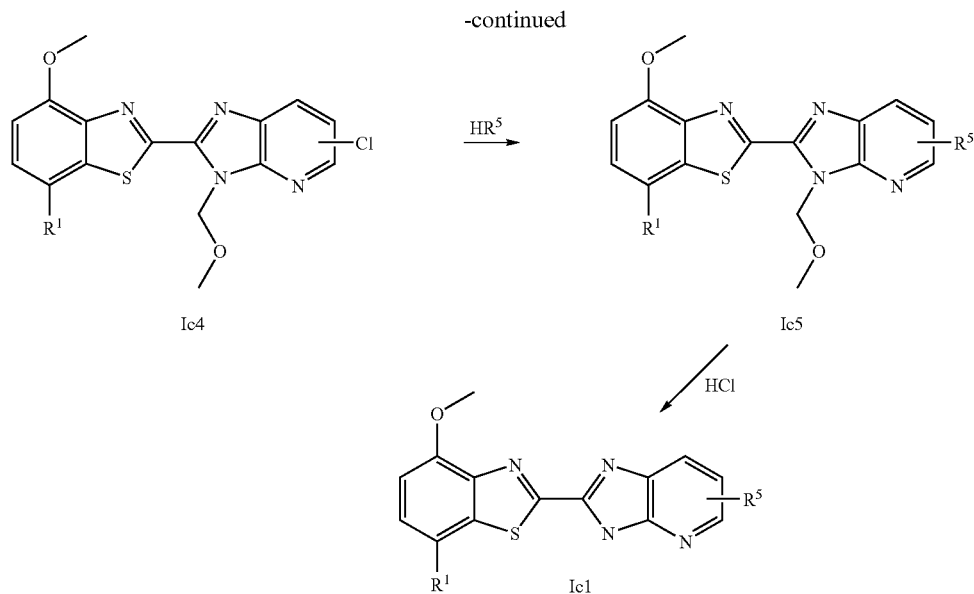

wherein $R^1$, $R^5$ and R' and R'' are as described above and MOMCl is methoxymethylchloride.

In accordance with scheme 5, 5-chloro-2-(4-methoxy-7-morpholin-4-yl-benzothiazol-2-yl)-3H-imidazo[4,5-b]pyridine (for $R^1$=morpholinyl, Ic2) was dissolved in a corresponding amine in an autoclave and heated to about 200° C. for 16 h. The residue was triturated in water whereupon the precipitate was isolated and worked up to obtain, for example, [2-(4-methoxy-7-morpholin-4-yl-benzothiazol-2-yl)-3H-imidazo[4,5-b]pyridin-5-yl]-dimethyl-amine (for R', R''=methyl, Ic3).

Furthermore, 5-chloro-2-(4-methoxy-7-morpholin-4-yl-benzothiazol-2-yl)-3H-imidazo[4,5-b]pyridine (for $R^1$=morpholinyl, Ic2) was dissolved in dry DMF and treated with NaH at 0° C. After stirring at ambient temperature for 1 h MOMCl and tetrabutyl ammonium iodide were added and the reaction mixture was stirred for about 16 h. The suspension was worked up to obtain the corresponding 5-chloro-3-methoxymethyl-2-(4-methoxy-7-morpholin-4-yl-benzothiazol-2-yl)-3H-imidazo[4,5-b]pyridine (Ic4), which was dissolved in morpholine (for $R^5$=morpholin) in an autoclave and heated to about 150° C. for 16 h. The residue was triturated in water whereupon the precipitate was worked up to obtain the corresponding 3-methoxymethyl-2-(4-methoxy-7-morpholin-4-yl-benzothiazol-2-yl)-5-morpholin-4-yl-3H-imidazo[4,5-b]pyridine (Ic5). The corresponding 2-(4-methoxy-7-morpholin-4-yl-benzothiazol-2-yl)-5-morpholin-4-yl-3H-imidazo[4,5-b]pyridine (Ic1) was obtained by treating with HCl for about 1.5 h.

Scheme 6

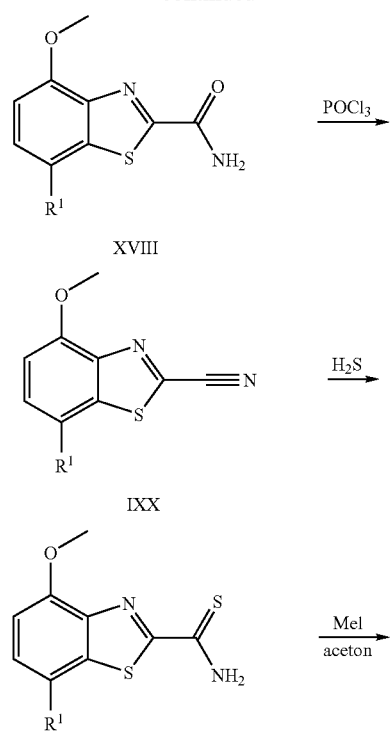

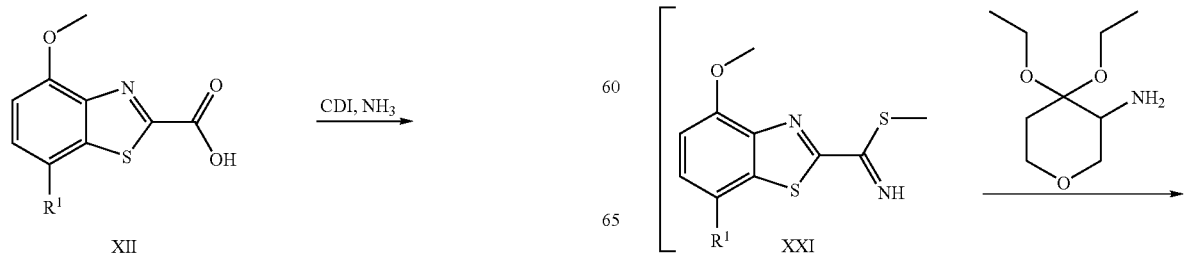

4,4-Diethoxy-tetrahydro-pyran-3-ylamine was prepared in accordance with scheme 7 in a conventional manner.

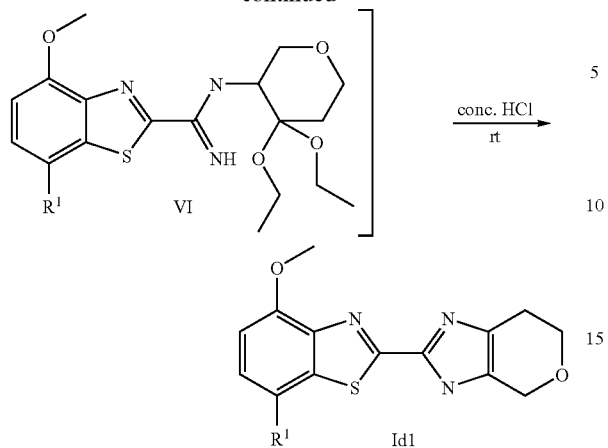

wherein R¹ is as described above.

In accordance with scheme 6, to a solution of 4-methoxy-7-morpholin-4-yl-benzothiazole-2-carboxylic acid (for R¹=morpholinyl, XII) and imidazole in pyridine was added at 0° C. phosphoroxychloride. After about 5 hours, the cold solution was diluted with ethylacetate and worked up in conventional manner to obtain 4-methoxy-7-morpholin-4-yl-benzothiazole-2-carbonitrile (IXX), which was dissolved in triethylamine and in pyridine and was then stirred for 4 hours with hydrogen sulfide at room temperature. Solvent and excess hydrogen sulfide were removed. The obtained 4-methoxy-7-morpholin-4-yl-benzothiazole-2-carbothioic acid amide (XX) was dissolved in tetrahydrofurane and was reacted with iodomethane at 50° C. for about 4 hours. All volatile components were distilled off under vacuum and the residue was dissolved in a solution of 4,4-diethoxy-tetrahydro-pyran-3-ylamine in tetrahydrofurane. The mixture was stirred at 50° C. overnight, the solvent was distilled off and the residue was suspended in hydrochloric acid and stirred for about 3 hours at room temperature. It was obtained (4-methoxy-7-morpholin-4-yl-benzothiazol-2-yl)-3,4,6,7-tetrahydro-pyrano[3,4-d]imidazole Id1).

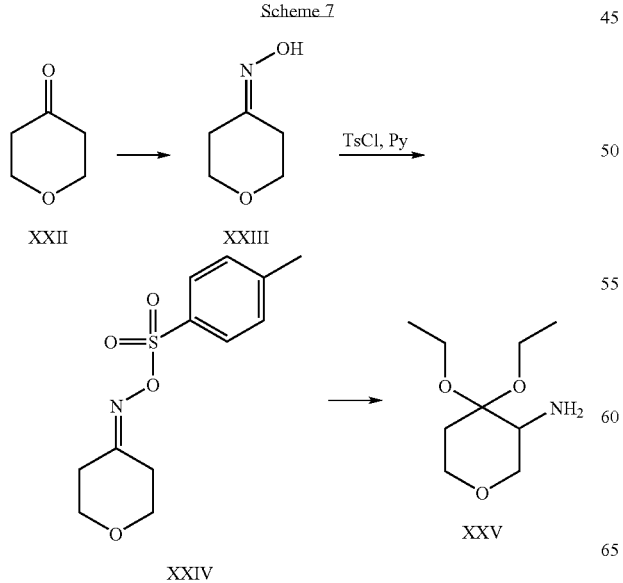

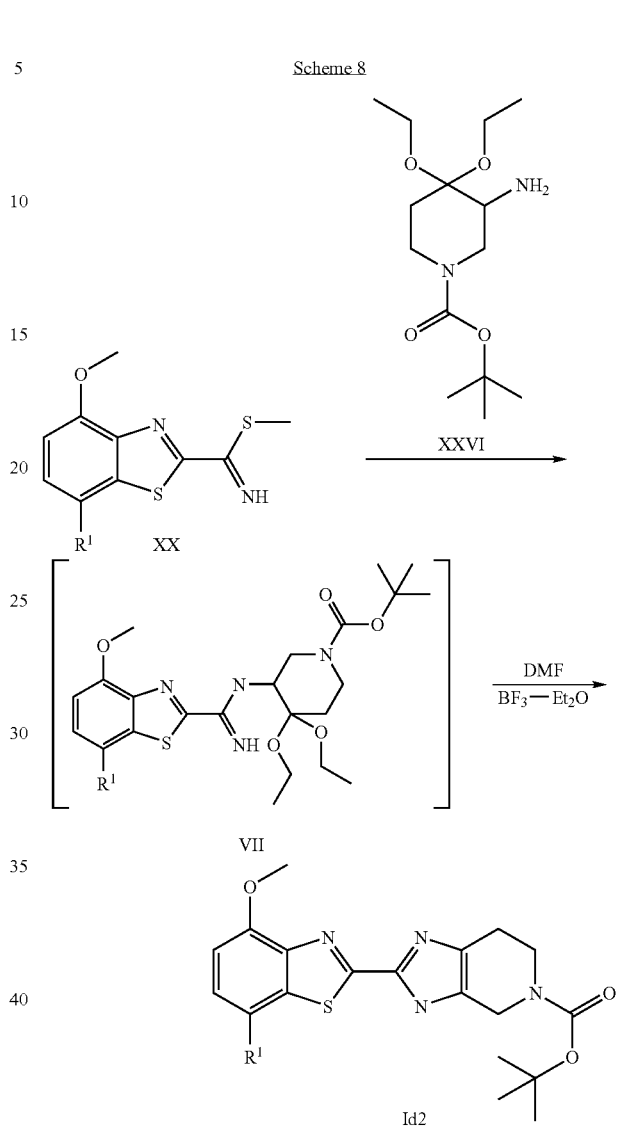

wherein R¹ is as described above.

In accordance with scheme 8,4-methoxy-7-morpholin-4-yl-benzothiazole-2-carbothioic acid amide (XX) and iodomethane in tetrahydrofurane were stirred at room temperature for three days. The resulting precipitate was filtered to yield 4-methoxy-7-morpholin-4-yl-benzothiazole-2-carboximidothioic acid methyl ester hydroiodide. To a solution of 4-methoxy-7-morpholin-4-yl-benzothiazole-2-carboximidothioic acid methyl ester hydroiodide in tetrahydrofurane was added 3-amino-4,4-diethoxy-piperidine-1-carboxylic acid tert-butyl ester (XXVI) and the mixture was stirred at room temperature for two days. Then boron trifluoride etherate was added and the solvent is distilled off under vacuum. Again boron trifluoride etherate was added and the mixture was dissolved in dimethylformamide and heated for 10 minutes at 125° C. It was obtained 2-(4-methoxy-7-morpholin-4-yl-benzothiazol-2-yl)-3,4,6,7-tetrahydro-imidazo[4,5-c]pyridine-5-carboxylic acid tert-butyl ester (Id2).

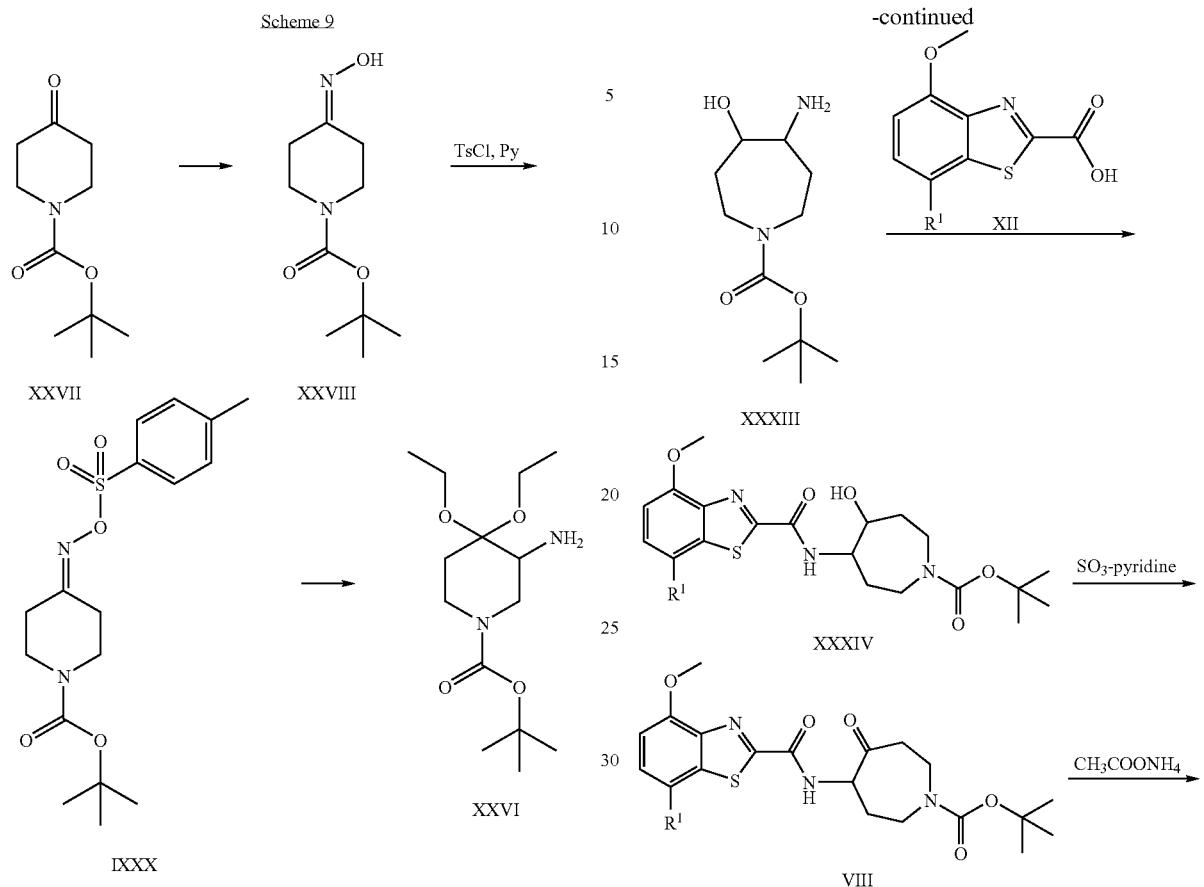

3-Amino-4,4-diethoxy-piperidine-1-carboxylic acid tert-butyl ester was prepared in accordance with scheme 9 in a conventional manner.

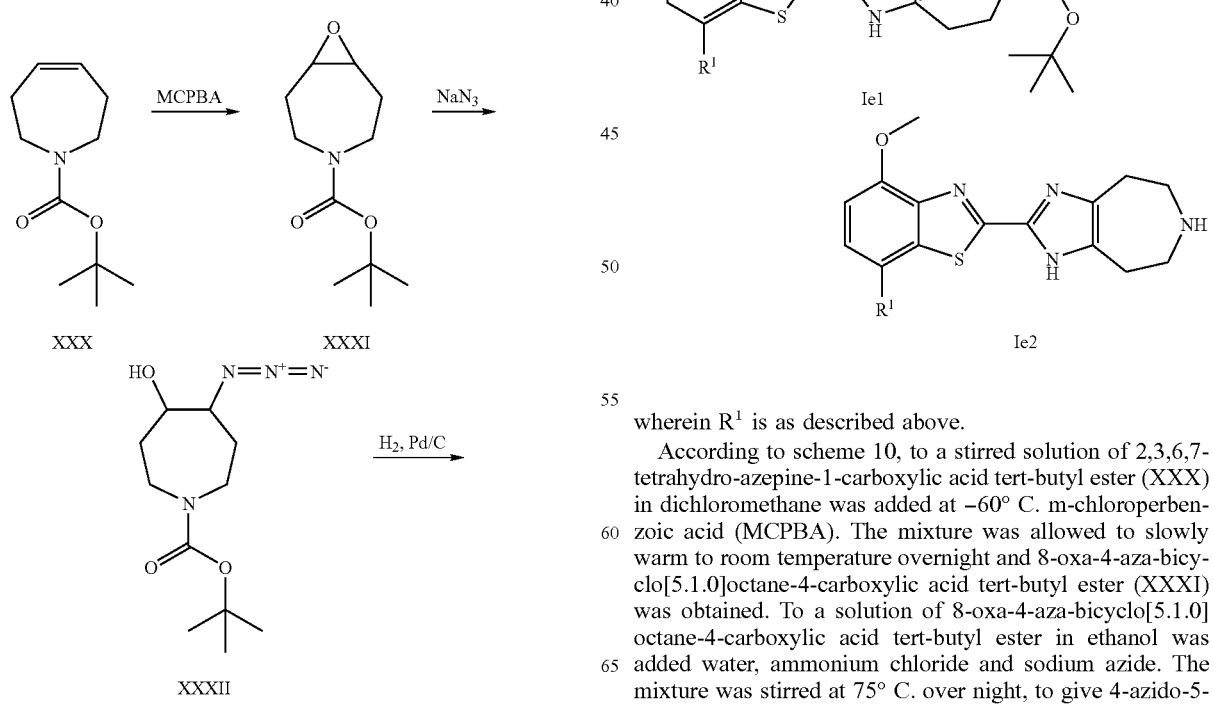

wherein $R^1$ is as described above.

According to scheme 10, to a stirred solution of 2,3,6,7-tetrahydro-azepine-1-carboxylic acid tert-butyl ester (XXX) in dichloromethane was added at −60° C. m-chloroperbenzoic acid (MCPBA). The mixture was allowed to slowly warm to room temperature overnight and 8-oxa-4-aza-bicyclo[5.1.0]octane-4-carboxylic acid tert-butyl ester (XXXI) was obtained. To a solution of 8-oxa-4-aza-bicyclo[5.1.0]octane-4-carboxylic acid tert-butyl ester in ethanol was added water, ammonium chloride and sodium azide. The mixture was stirred at 75° C. over night, to give 4-azido-5-hydroxy-azepane-1-carboxylic acid tert-butyl ester (XXXII). 4-Azido-5-hydroxy-azepane-1-carboxylic acid tert-butyl ester in methanol was hydrogenated in the presence of palladium on charcoal (10%) to yield 4-amino-5-hydroxy-azepane-1-carboxylic acid tert-butyl ester (XXXIII). 4-Methoxy-7-morpholin-4-yl-benzothiazole-2-carboxylic acid and 1,1'-carbonyl-diimidazole in dimethylformamide are stirred at room temperature for about 16 hours. 4-Amino-5-hydroxy-azepane-1-carboxylic acid tert-butyl ester was added and stirring was continued for 16 hours at room temperature. It was obtained 4-hydroxy-5-[(4-methoxy-7-morpholin-4-yl-benzothiazole-2-carbonyl)-amino]-azepane-1-carboxylic acid tert-butyl ester (XXXIV). To a solution of 4-hydroxy-5-[(4-methoxy-7-morpholin-4-yl-benzothiazole-2-carbonyl)-amino]-azepane-1-carboxylic acid tert-butyl ester in dimethylsulfoxide was added triethylamine, dichloromethane and a solution of sulfur trioxide pyridine complex in dimethylsulfoxide. The mixture was stirred for 18 hours at room temperature. After purification 4-[(4-methoxy-7-morpholin-4-yl-benzothiazole-2-carbonyl)-amino]-5-oxo-azepane-1-carboxylic acid tert-butyl ester (VIII) was obtained.

A mixture of 4-[(4-methoxy-7-morpholin-4-yl-benzothiazole-2-carbonyl)-amino]-5-oxo-azepane-1-carboxylic acid tert-butyl ester and ammonium acetate (VIII) was melted at 120° C. for 3 hours and cooled to room temperature. It was obtained 2-(4-methoxy-7-morpholin-4-yl-benzothiazol-2-yl)-4,5,7,8-tetrahydro-1H-imidazo[4,5-d]azepine-6-carboxylic acid tert-butyl ester (Ie1).

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the Preparations and Examples herein below. However, other equivalent separation or isolation procedures could, of course, also be used.

Salts of Compounds of Formula I

The compounds of formula I may be basic, for example in cases where the residue R contains a basic group such as an aliphatic or aromatic amine moiety. In such cases the compounds of Formula I may be converted to a corresponding acid addition salt.

The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically usable addition salts possess valuable pharmacological properties. Specifically, it has been found that the compounds of the present invention are adenosine receptor ligands and possess a high affinity towards the adenosine $A_{2A}$ receptor and a good selectivity towards $A_1$ and $A_3$ receptors.

The compounds were investigated in accordance with the tests given hereinafter.

Human Adenosine $A_1$ receptor

The human adenosine $A_1$ receptor was recombinantly expressed in Chinese hamster ovary (CHO) cells using the semliki forest virus expression system. Cells were harvested, washed twice by centrifugation, homogenized and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-DPCPX (([propyl-$^3$H]8-cyclopentyl-1,3-dipropyxanthine); 0.6 nM) binding assay was carried out in 96-well plates in the presence of 2.5 µg of membrane protein, 0.5 mg of Ysi-poly-1-lysine SPA beads and 0.1 U adenosine deaminase in a final volume of 200 µl of buffer A. Non-specific binding was defined using xanthine amine congener (XAC; 2 µM). Compounds were tested at 10 concentrations from 10 µM–0.3 nM. All assays were conducted in duplicate and repeated at least two times. Assay plates were incubated for 1 hour at room temperature before centrifugation and then bound ligand determined using a Packard Topcount scintillation counter. $IC_{50}$ values were calculated using a non-linear curve fitting program and Ki values calculated using the Cheng-Prussoff equation.

Human Adenosine $A_{2A}$ Receptor

The human adenosine $A_{2A}$ receptor was recombinantly expressed in Chinese hamster ovary (CHO) cells using the semliki forest virus expression system. Cells were harvested, washed twice by centrifugation, homogenized and again washed by centrifugation. The final washed membrane pellet was suspended in a Tris (50 mM) buffer containing 120 mM NaCl, 5 mM KCl, 2 mM $CaCl_2$ and 10 mM $MgCl_2$ (pH 7.4) (buffer A). The [$^3$H]-SCH-58261 (Dionisotti et al., 1997, Br J Pharmacol 121, 353; 1 nM) binding assay was carried out in 96-well plates in the presence of 2.5 µg of membrane protein, 0.5 mg of Ysi-poly-1-lysine SPA beads and 0.1 U adenosine deaminase in a final volume of 200 µl of buffer A. Non-specific binding was defined using xanthine amine congener (XAC; 2 µM). Compounds were tested at 10 concentrations from 10 µM-0.3 nM. All assays were conducted in duplic and repeated at least two times. Assay plates were incubated for hour at room temperature before centrifugation and then bound ligand determined using a Packard Topcount scintillation counter. $IC_{50}$ values were calculated using a non-linear curve fitting program and Ki values calculated using the Cheng-Prussoff equation.

It has been shown that compounds of formula I have a good affinity to the $A_{2A}$ receptor and a high selectivity toward the $A_1$. The present compounds show a pKi>7.0.

| Example No. Type of compounds | $hA_1$ (pKi) | $hA_2$ (pKi) |
|---|---|---|
| 1 Ia | 6.0 | 7.9 |
| 4 Ia | 6.7 | 8.3 |

-continued

| Example No. Type of compounds | hA$_1$ (pKi) | hA$_2$ (pKi) |
|---|---|---|
| 20 Ia | 5.1 | 7.3 |
| 2 Ib | 6.8 | 9.3 |
| 3 Ib | 5.1 | 7.0 |
| 6 Ic | 57 | 8.5 |
| 9 Ic | 5.1 | 8.6 |
| 14 Ic | 5.6 | 8.5 |
| 22 Id | 6.1 | 8.6 |
| 23 Id | 6.4 | 8.9 |
| 26 Ie | 6.2 | 9.0 |
| 28 Ie | 5.8 | 8.9 |
| 30 Ie | 5.9 | 8.8 |

The compounds of formula I and the pharmaceutically acceptable salts of the compounds of formula I can be used as medicaments, e.g., in the form of pharmaceutical preparations. The pharmaceutical preparations can be administered orally, e.g., in the form of tablets, coated tablets, dragees, hard and soft gelatin capsules, solutions, emulsions or suspensions. The administration can, however, also be effected rectally, e.g. in the form of suppositories, parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Medicaments containing a compound of formula I or a pharmaceutically acceptable salt thereof and a therapeutically inert carrier are also an aspect of the present invention, as is a process for their production, which comprises bringing one or more compounds of formula I and/or pharmaceutically acceptable salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents and for the production of corresponding medicaments.

Highly preferred indications in accordance with the present invention are those, which include disorders of the central nervous system, for example the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day for an adult weighing 70 kg of a compound of general formula I or of the corresponding amount of a pharmaceutically acceptable salt thereof. The daily dosage may be administered as single dose or in divided doses and, in addition, the upper limit can also be exceeded when this is found to be indicated.

| | | Tablet Formulation (Wet Granulation) mg/tablet | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

| | | Capsule Formulation mg/capsule | | | |
|---|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

The following preparation and examples illustrate the invention but are not intended to limit its scope.

EXAMPLE 1

2-(1H-Imidazol-2-yl)-4-methoxy-7-morpholin-4-yl-benzothiazole

To a suspension of 1.0 g of imidazole-2-carboxylic acid (8.9 mmol) in 15 ml DMF was added 1.6 g of CDI (9.8 mmol) and stirred at ambient temperature for 1 h. Then the mixture was refluxed for 30 min. After cooling to ambient temperature, 2.0 g of 2-methoxy-5-morpholin-4-yl-phenylamine (9.8 mmol) were added and the reaction mixture was heated to reflux for 16 h. The mixture was evaporated and the residue taken up in water (40 ml) and extracted 3 times with ethyl acetate. The combined organic phases were dried on sodium carbonate, evaporated and the residue subjected to column chromatography (silica gel, ethyl acetate/hexanes 2:1). 0.25 g 1H-imidazole-2-carboxylic acid (2-methoxy-5-morpholin-4-yl-phenyl)-amide (9%) were obtained as a white solid; M.p.: 227–230° C. 0.2 g of 1H-Imidazole-2-carboxylic acid (2-methoxy-5-morpholin-4-yl-phenyl)-amide (0.66 mmol) were taken up in toluene (8.0 ml) and treated with 0.8 g of Lawesson reagent (2.0 mmol). The reaction mixture was heated to reflux for 22 h. After cooling to ambient temperature, water (25 ml) was added and the mixture was extracted 3 times with ethyl acetate. The combined organic phases were dried on sodium carbonate, evaporated and the residue subjected to column chromatography (silica gel, ethyl acetate/hexanes 1:1). 0.125 g of 1H-imidazole-2-carbothioic acid (2-methoxy-5-morpholin-4-yl-phenyl)-amide (59%) was obtained as a yellow foam; MS (ISP): m/e=319 (M+H$^+$).

0.08 g of 1H-Imidazole-2-carbothioic acid (2-methoxy-5-morpholin-4-yl-phenyl)-amide (0.25 mmol) were taken up in water (2.0 ml) and treated with 0.056 g KOH (1.0 mmol) and 0.331 g of potassium hexacyano ferrate (1.0 mmol) at reflux for 1 h. After cooling to ambient temperature water (10 ml) was added and the mixture was filtered. The residue on the filter was dried in vacuo at 40° C. One obtained 0.037 g of 2-(1H-imidazol-2-yl)-4-methoxy-7-morpholin-4-yl-benzothiazole (47%) as a yellow solid; M.p.: 228–230° C.

EXAMPLE 2

2-(1H-Benzoimidazol-2-yl)-4-methoxy-7-morpholin-4-yl-benzothiazole

To a suspension of 0.19 g of benzoimidazole-2-carboxylic acid (1.0 mmol) in 4 ml DMF was added 0.21 g of CDI (1.3 mmol) and stirred at ambient temperature for 1 h. Then the mixture was refluxed for 30 min. After cooling to ambient temperature, 0.25 g of 2-methoxy-5-morpholin-4-yl-phenylamine (1.2 mmol) was added and the reaction mixture was heated to reflux for 16 h. The mixture was evaporated and the residue taken up in water (40 ml) and extracted 3 times with methylene chloride. The combined organic phases were dried on sodium carbonate, evaporated and the residue was stirred in hot ethyl acetate. After filtration and trying 0.27 g 1H-benzoimidazole-2-carboxylic acid (2-methoxy-5-morpholin-4-yl-phenyl)-amide (63%) were obtained as a yellow solid; M.p.: 236–237° C. 0.2 g of 1H-Benzoimidazole-2-carboxylic acid (2-methoxy-5-morpholin-4-yl-phenyl)-amide (0.71 mmol) was taken up in toluene (15.0 ml) and treated with 0.28 g of Lawesson reagent (0.71 mmol). The reaction mixture was heated to reflux for 2 h. After cooling to ambient temperature, water (25 ml) was added and the mixture was extracted 3 times with ethyl acetate. The combined organic phases were dried on sodium carbonate, evaporated and the residue subjected to column chromatography (silica gel, ethyl acetate/hexanes 1:2, then ethyl acetate). 0.22 g of 1H-Benzoimidazole-2-carbothioic acid (2-methoxy-5-morpholin-4-yl-phenyl)-amide (86%) was obtained as a yellow solid; M.p.: 240–241° C. 0.19 g of 1H-Benzoimidazole-2-carbothioic acid (2-methoxy-5-morpholin-4-yl-phenyl)-amide (0.52 mmol) were taken up in water (5.0 ml) and treated with 0.116 g KOH (2.0 mmol) and 0.68 g of potassium hexacyano ferrate (2.0 mmol) at reflux for 24 h. After cooling to ambient temperature water (10 ml) was added and the mixture was filtered. The residue on the filter was dissolved in methanol and subjected to column chromatography (silica gel, methylene chloride/methanol 99:1). One obtained 0.089 g of 2-(1H-benzoimidazol-2-yl)-4-methoxy-7-morpholin-4-yl-benzothiazole (39%) as a yellow solid; M.p.: 284–286° C.

EXAMPLE 3

4-Methoxy-2-(1-methyl-1H-benzoimidazol-2-yl)-7-morpholin-4-yl-benzothiazole 0.05 g of 2-(1H-Benzoimidazol-2-yl)-4-methoxy-7-morpholin-4-yl-benzothiazole (0.14 mmol) were dissolved in dry DMF (2.0 ml) and treated with 0.005 g NaH (65% in oil, 0.14 mmol) at 0° C. After stirring at ambient temperature for 1 h, 25 µl MeI (0.4 mmol) was added and the reaction mixture was stirred for 16 h. The suspension was filtered and the residue on the filter dried in vacuo. One obtained 0.042 g of 4-methoxy-2-(1-methyl-1H-benzoimidazol-2-yl)-7-morpholin-4-yl-benzothiazole (81%) as a yellow solid; M.p.: 283–285° C.

EXAMPLE 4

2-(1H-Imidazol-2-yl)-4-methoxy-7-phenyl-benzothiazole

To a suspension of 0.31 g of imidazole-2-carboxylic acid (2.76 mmol) in 14 ml DMF was added 0.448 g of CDI (2.76 mmol), 0.38 ml triethylamine (2.76 mmol) and stirred at ambient temperature for 1 h. Then the mixture was refluxed for 30 min. After cooling to ambient temperature, 0.5 g of 5-phenyl-o-anisidine (2.5 mmol) was added and the reaction mixture was heated to reflux for 16 h. The mixture was evaporated and the residue taken up in water (40 ml) and extracted 3 times with methylene chloride. The combined organic phases were tried on sodium carbonate, evaporated and the residue was stirred in hot ethyl acetate. After filtration and drying, 0.11 g 1H-imidazole-2-carboxylic acid (4-methoxy-biphenyl-3-yl)-amide (14%) were obtained as a light yellow solid; M.p.: 276° C. 0.1 g of 1H-Imidazole-2-carboxylic acid (4-methoxy-biphenyl-3-yl)-amide (0.36 mmol) was taken up in toluene (5.0 ml) and treated with 0.435 g of Lawesson reagent (1.0 mmol). The reaction mixture was heated to reflux for 16 h. After cooling to ambient temperature, water (25 ml) was added and the mixture was extracted 3 times with dichloro methane. The combined organic phases were dried on sodium carbonate, evaporated and the residue triturated in methanol. 0.08 g of 1H-imidazole-2-carbothioic acid (4-methoxy-biphenyl-3-yl)-amide (73%) were obtained as a yellow solid; M.p.: 223–226° C.

0.049 g of 1H-Imidazole-2-carbothioic acid (4-methoxy-biphenyl-3-yl)-amide (0.16 mmol) was taken up in chloroform and treated with 8.1 µl of Br$_2$ (0.16 mmol) for 4 h at reflux. Then the reaction was quenched with sodium thiosulfate (38%) and extracted with chloroform. The combined organic phases were dried on sodium sulfate, filtered and evaporated. The residue was subjected to column chromatography (silica gel, methylene chloride/methanol 40:1) to yield 0.016 g of 2-(1H-imidazol-2-yl)-4-methoxy-7-phenyl-benzothiazole (33%) as a colorless solid; M.p.: 205–206° C.

EXAMPLE 5

2-(4-Methoxy-7-morpholin-4-yl-benzothiazol-2-yl)-5-methyl-3H-imidazo[4,5-b]pyridine 0.5 g 2,3-Diamino-6-methyl pyridine (4.0 mmol) and 0.37 g glycolic acid were heated at 150° C. for 1 h. The residue was suspended in chloroform (7.0 ml) treated with 1.5 ml thionyl chloride (20 mmol)for 4 h at reflux. The mixture was evaporated and the residue triturated with methanol. After concentration the residue was stirred over night in ether and the suspension was then filtered. The residue on the filter was dried to yield 0.67 g 2-chloromethyl-5-methyl-3H-imidazo[4,5-b]pyridine hydrochloride as a dark brown solid; M.p.: 225–230° C., (dec.).

1.7 ml Triethyl amine (12.0 mmol), 0.19 g sulfur (6.0 mmol) and 0.65 g 2-chloromethyl-5-methyl-3H-imidazo[4,5-b]pyridine hydrochloride (3.0 mmol) were dissolved in DMF (2 ml) and stirred at ambient temperature for 2 h. After cooling to 0° C., 0.18 ml MeI (3.0 mmol) were added and stirring at ambient temperature was continued for 1 h. Then water (20 ml) was added and the mixture extracted 3 times with ethyl acetate (30 ml). The combined organic phase were filtered over dicalit® and concentrated. The residue was dissolved in ethanol (7 ml) and treated with 0.3 g 2-methoxy-5-morpholin-4-yl-phenylamine (1.45 mmol) for 16 h at reflux. Upon cooling to ambient temperature a precipitate formed, which was isolated and dried in vacuo. 0.14 g 5-methyl-3H-imidazo[4,5-b]pyridine-2-carbothioic acid (2-methoxy-5-morpholin-4-yl-phenyl)-amide (25%) were obtained as a light red solid; M.p.: 189–191° C.

0.3 g 5-Methyl-3H-imidazo[4,5-b]pyridine-2-carbothioic acid (2-methoxy-5-morpholin-4-yl-phenyl)-amide (0.8 mmol) was dissolved in ethyl acetate (3 ml), heated to reflux and treated with 0.27 ml HBr in AcOH (5.7M, 1.6 mmol) and 0.067 ml DMSO (0.94 mmol). Stirring at reflux was continued for 2 h. Upon cooling a precipitation formed, which was isolated and dissolved in water (2 ml). The pH was adjusted to 10 with 25% ammonium hydroxide in water. Once again a precipitation formed, which was filtered. The residue on the filter was washed with water and dried in vacuo. One obtained 0.125 g 2-(4-methoxy-7-morpholin-4-yl-benzothiazol-2-yl)-5-methyl-3H-imidazo[4,5-b]pyridine (42%) as a yellow solid; M.p.: 200–210° C.

EXAMPLE 6

5-Chloro-2-(4-methoxy-7-morpholin-4-yl-benzothiazol-2-yl)-3H-imidazo[4,5-b]pyridine 1.0 g 2-Hydroxymethyl-5-chloro-3H-imidazo[4,5-b]pyridine (5.45 mmol) was suspended in chloroform (10.0 ml) and treated with 3.3 ml thionyl chloride (45 mmol) for 4 h at reflux. The mixture was evaporated and the residue triturated with methanol. After concentration the residue was stirred over night in ether and the suspension was then filtered. The residue on the filter was dried to yield 0.67 g 5-chloro-2-chloromethyl-3H-imidazo[4,5-b]pyridine hydrochloride as a brown solid; M.p.: 218–220° C., (dec.). 14.5 ml Triethyl amine (104.0 mmol), 1.67 g sulfur (52.0 mmol) and 0.65 g 5-chloro-2-chloromethyl-3H-imidazo[4,5-b]pyridine hydrochloride (26.0 mmol) were dissolved in DMF (15 ml) and stirred at ambient temperature for 2 h. After cooling to 0° C., 1.6 ml MeI (26.0 mmol) were added and stirring at ambient temperature was continued for 1 h. Then water (100 ml) was added and the mixture extracted 3 times with ethyl acetate (150 ml). The combined organic phase were filtered over dicalit® and concentrated. The residue was dissolved in ethanol (100 ml) and treated with 5.4 g 2-methoxy-5-morpholin-4-yl-phenylamine (26 mmol) for 16 h at reflux. Upon cooling to ambient temperature a precipitate formed, which was isolated and dried in vacuo. 2 g 5-chloro-3H-imidazo[4,5-b]pyridine-2-carbothioic acid (2-methoxy-5-morpholin-4-yl-phenyl)-amide (19%) was obtained as a red solid; MS (ISP): m/e=404 (M+H$^+$).

1.0 g 5-Chloro-3H-imidazo[4,5-b]pyridine-2-carbothioic acid (2-methoxy-5-morpholin-4-yl-phenyl)-amide (2.5 mmol) was dissolved in ethyl acetate (7 ml), heated to reflux and treated with 0.87 ml HBr in AcOH (5.7M, 5.0 mmol) and 0.2 ml DMSO (3.0 mmol). Stirring at reflux was continued for 2 h. Upon cooling a precipitation formed, which was isolated and dissolved in water (2 ml). The pH was adjusted to 10 with 25% ammonium hydroxide in water. Once again a precipitation formed, which was filtered. The residue on the filter was washed with water and dried in vacuo. One obtained 0.91 g 5-chloro-2-(4-methoxy-7-morpholin-4-yl-benzothiazol-2-yl)-3H-imidazo[4,5-b]pyridine (92%) as a yellow solid; M.p.: >300° C. (dec.).

EXAMPLE 7

5-Chloro-3-methoxymethyl-2-(4-methoxy-7-morpholin-4-yl-benzothiazol-2-yl)-3H-imidazo[4,5-b]pyridine 0.3 g 5-Chloro-2-(4-methoxy-7-morpholin-4-yl-benzothiazol-2-yl)-3H-imidazo[4,5-b]pyridine (0.74 mmol) was dissolved in dry DMF (10.0 ml) and treated with 0.033 g NaH (65% in oil, 0.9 mmol) at 0° C. After stirring at ambient temperature for 1 h, 68 μl MOMCl (0.9 mmol) and 0.011 g tetrabutyl ammonium iodide (0.03 mmol) were added and the reaction mixture was stirred for 16 h. The suspension was filtered and the residue triturated in ether. Upon drying in vacuo, one obtained 0.29 g of 5-chloro-3-methoxymethyl-2-(4-methoxy-7-morpholin-4-yl-benzothiazol-2-yl)-3H-imidazo[4,5-b]pyridine (87%) as a yellow solid; M.p.: 167–170° C.

EXAMPLE 8

3-Methoxymethyl-2-(4-methoxy-7-morpholin-4-yl-benzothiazol-2-yl)-5-morpholin-4-yl-3H-imidazo[4,5-b]pyridine g 5-Chloro-3-methoxymethyl-2-(4-methoxy-7-morpholin-4-yl-benzothiazol-2-yl)-3H-imidazo[4,5-b]pyridine (0.22 mmol) were dissolved in morpholine (5 ml) in an autoclave and heated to 150° C. for 16 h. The residue was triturated in water whereupon a precipitate formed, which was isolated and dried in vacuo. 0.074 g 3-methoxymethyl-2-(4-methoxy-7-morpholin-4-yl-benzothiazol-2-yl)-5-morpholin-4-yl-3H-imidazo[4,5-b]pyridine (66%) were obtained as a yellow solid; M.p.: 126–128° C.

EXAMPLE 9

2-(4-Methoxy-7-morpholin-4-yl-benzothiazol-2-yl)-5-morpholin-4-yl-3H-imidazo[4,5-b]pyridine 0.065 g 3-Methoxymethyl-2-(4-methoxy-7-morpholin-4-yl-benzothiazol-2-yl)-5-morpholin-4-yl-3H-imidazo[4,5-b]pyridine (0.13 mmol) was treated with 5N HCl (2 ml) at 90° C. for 1.5 h. The reaction mixture was concentrated, taken up in water (3 ml) and adjusted to pH 10 with ammonium hydroxide (25%), whereupon a precipitation formed. The precipitation was filtered and the crystals were triturated in hot ethanol. After drying in vacuo 0.036 g 2-(4-methoxy-7-morpholin-4-yl-benzothiazol-2-yl)-5-morpholin-4-yl-3H-imidazo[4,5-b]pyridine (61%) was obtained as a yellow solid; M.p.: 260–262° C.

EXAMPLE 10

3-Methoxymethyl-2-(4-methoxy-7-morpholin-4-yl-benzothiazol-2-yl)-5-pyrrolidin-1-yl-3H-imidazo[4,5-b]pyridine 0.1 g 5-Chloro-3-methoxymethyl-2-(4-methoxy-7-morpholin-4-yl-benzothiazol-2-yl)-3H-imidazo[4,5-b]pyridine (0.22 mmol) was dissolved in pyrrolidine (5 ml) in an autoclave and heated to 130° C. for 16 h. The residue was triturated in water whereupon a precipitate formed, which was isolated and dried in vacuo. 0.08 g 3-methoxymethyl-2-(4-methoxy-7-morpholin-4-yl-benzothiazol-2-yl)-5-pyrrolidin-4-yl-3H-imidazo[4,5-b]pyridine (74%) were obtained as a yellow solid; M.p.: 120–130° C.

EXAMPLE 11

2-(4-Methoxy-7-morpholin-4-yl-benzothiazol-2-yl)-5-pyrrolidin-1-yl-3H-imidazo[4,5-b]pyridine 0.07 g 3-Methoxymethyl-2-(4-methoxy-7-morpholin-4-yl-benzothiazol-2-yl)-5-morpholin-4-yl-3H-imidazo[4,5-b]pyridine (0.15 mmol) was treated with 5N HCl (2 ml) at 90° C. for 1.5 h. The reaction mixture was concentrated, taken up in water (3 ml) and adjusted to pH 10 with ammonium hydroxide (25%), whereupon a precipitation formed. The precipitation was filtered and the crystals were triturated in hot ethanol. After drying in vacuo 0.025 g 2-(4-methoxy-7-morpholin-4-yl-benzothiazol-2-yl)-5-pyrrolidin-4-yl-3H-imidazo[4,5-b]pyridine (39%) was obtained as a yellow solid; M.p.: 264–268° C.

EXAMPLE 12

[2-(4-Methoxy-7-morpholin-4-yl-benzothiazol-2-yl)-3H-imidazo[4,5-b]pyridin-5-yl]-dimethyl-amine 0.03 g 5-Chloro-2-(4-methoxy-7-morpholin-4-yl-benzothiazol-2-yl)-3H-imidazo[4,5-b]pyridine (0.07 mmol) was dissolved in dimethylamine (5 ml) in an autoclave and heated to 200° C. for 16 h. The residue was triturated in water whereupon a precipitate formed, which was isolated and dried in vacuo. 0.08 g [2-(4-Methoxy-7-morpholin-4-yl-benzothiazol-2-yl)-3H-imidazo[4,5-b]pyridin-5-yl]-dimethyl-amine (29%) were obtained as a brown solid; M.p.: 120–130° C.

EXAMPLE 13

1-[2-(4-Methoxy-7-morpholin-4-yl-benzothiazol-2-yl)-3H-imidazo[4,5-b]pyridin-5-yl]-piperidin-4-ol 0.05 g 5-Chloro-2-(4-methoxy-7-morpholin-4-yl-benzothiazol-2-yl)-3H-imidazo[4,5-b]pyridine (0.11 mmol), 0.034 g 4-hydroxypiperidine (0.34 mmol), 1 mg DMAP and 0.4 ml Hünigs base (2.2 mmol) were dissolved in NMP (1 ml). After stirring for 72 h at 120° C., the reaction mixture was concentrated and the residue taken up in water. A precipitation formed, which was filtered and dried in vacuo to yield 0.04 g 1-[3-methoxymethyl-2-(4-methoxy-7-morpholin-4-yl-benzothiazol-2-yl)-3H-imidazo[4,5-b]pyridin-5-yl]-piperidin-4-ol (70%) as a light brown solid; M.p.: 120–130° C.

0.035 g 1-[3-Methoxymethyl-2-(4-methoxy-7-morpholin-4-yl-benzothiazol-2-yl)-3H-imidazo[4,5-b]pyridin-5-yl]-piperidin-4-ol (0.07 mmol) was treated with 5N HCl (1 ml) at 90° C. for 0.5 h. The reaction mixture was concentrated, taken up in water (1 ml) and adjusted to pH 10 with ammonium hydroxide (25%), whereupon a precipitation formed. The precipitation was filtered and the crystals were triturated in hot ethanol. After drying in vacuo 0.018 g 1-[2-(4-methoxy-7-morpholin-4-yl-benzothiazol-2-yl)-3H-imidazo[4,5-b]pyridin-5-yl]-piperidin-4-ol (56%) was obtained as a yellow solid; M.p.: 228–230° C.

EXAMPLE 14

[2-(4-Methoxy-7-morpholin-4-yl-benzothiazol-2-yl)-3H-imidazo[4,5-b]pyridin-5-yl]-methyl-(tetrahydro-pyran-4-ylmethyl)-amine 0.08 g 5-Chloro-2-(4-methoxy-7-morpholin-4-yl-benzothiazol-2-yl)-3H-imidazo[4,5-b]pyridine (0.18 mmol), 0.180g 4-(methylamino)-methyl-tetrahydro-pyran (1.08 mmol), 1 mg DMAP and 1.24 ml Hünigs base (7.2 mmol) were dissolved in NMP (1 ml). After stirring for 42 h at 150° C., the reaction mixture was concentrated and the residue taken up in water. A precipitation formed, which was filtered and crystallized from hot ethanol. After drying in vacuo 0.035 g [3-methoxymethyl-2-(4-methoxy-7-morpholin-4-yl-benzothiazol-2-yl)-3H-imidazo[4,5-b]pyridin-5-yl]-methyl-(tetrahydro-pyran-4-ylmethyl)-amine (36%) as a brown oil; MS (ISP): m/e=539 (M+H$^+$).

0.03 g [3-Methoxymethyl-2-(4-methoxy-7-morpholin-4-yl-benzothiazol-2-yl)-3H-imidazo[4,5-b]pyridin-5-yl]-methyl-(tetrahydro-pyran-4-ylmethyl)-amine (0.056 mmol) were treated with 5N HCl (1 ml) at 90° C. for 0.5 h. The reaction mixture was concentrated, taken up in water (1 ml) and adjusted to pH 10 with ammonium hydroxide (25%), whereupon a precipitation formed. The precipitation was filtered, the crystals washed with water. After drying in vacuo, 0.015 g [2-(4-methoxy-7-morpholin-4-yl-benzothiazol-2-yl)-3H-imidazo[4,5-b]pyridin-5-yl]-methyl-(tetrahydro-pyran-4-ylmethyl)-amine (55%) was obtained as a yellow solid; M.p.: 190–195° C.

EXAMPLE 15

4-Methoxy-7-morpholin-4-yl-2-(4-phenyl-1H-imidazol-2-yl)-benzothiazole 0.20 g 4-Methoxy-7-morpholin-4-yl-benzothiazole-2-carboxylic acid and 0.125 g 1,1'-carbonyl-diimidazole in 1 ml DMF were stirred at room temperature for 1 hour. 0.13 g 2-aminoacetophenone hydrochloride and 0.08 g triethylamine were added and stirring was continued for two days at room temperature. 200 ml water was added and the mixture was extracted with ethylacetate. Chromatography on silicagel with ethylacetate/hexane 4:6 yielded 0.18 g (64%) 4-methoxy-7-morpholin-4-yl-benzothiazole-2-carboxylic acid (2-oxo-2-phenyl-ethyl)-amide as a yellow solid; M.p.: 197–200° C.; MS (ISP): m/e=412 (M+H$^+$).

A mixture of 0.18 g 4-methoxy-7-morpholin-4-yl-benzothiazole-2-carboxylic acid (2-oxo-2-phenyl-ethyl)-amide and 0.57 g ammonium triflouroacetate was melted at 165° C. for 40 minutes and, after cooling to room temperature, suspended in water. Extraction with dichloromethane and chromatography on silicagel with ethylacetate/hexane 1:2 gave 0.07 g (41%) 4-methoxy-7-morpholin-4-yl-2-(4-phenyl-1H-imidazol-2-yl)-benzothiazole as yellow solid; M.p.: 226–233° C.; MS (ISP): m/e=393 (M+H$^+$).

EXAMPLE 16

2-[4-(2,3-Dihydro-benzo[1,4]dioxin-6-yl)-1H-imidazol-2-yl]-4-methoxy-7-morpholin-4-yl-benzothiazole 0.35 g 4-Methoxy-7-morpholin-4-yl-benzothiazole-2-carboxylic acid and 0.22 g 1,1'-carbonyl-diimidazole in 6 ml DMF were stirred at room temperature for 4 hours. 0.30 g 2-amino-1-(2,3-dihydro-benzo[1,4]dioxin-6-yl)-ethanone hydrochloride and 0.18 g triethylamine were added and stirring was continued over night at room temperature. 100 ml water was added and the mixture was extracted with ethylacetate. Chromatography on silicagel with ethylacetate/hexane 1:1 yielded 0.28 g (50%) 4-methoxy-7-morpholin-4-yl-benzothiazole-2-carboxylic acid [2-(2,3-dihydro-benzo[1,4]dioxin-6-yl)-2-oxo-ethyl]-amide as a yellow solid; M.p.: 206–208° C.; MS (ISP): m/e=470 (M+H$^+$).

A mixture of 0.19 g 4-methoxy-7-morpholin-4-yl-benzothiazole-2-carboxylic acid [2-(2,3-dihydro-benzo[1,4]dioxin-6-yl)-2-oxo-ethyl]-amide and 0.54 g ammonium triflouroacetate was melted at 175° C. for 45 minutes and, after cooling to room temperature, suspended in water. Extraction with dichloromethane and chromatography on silicagel with ethylacetate/hexane 6:4 gave 0.13 g (71%) 2-[4-(2,3-dihydro-benzo[1,4]dioxin-6-yl)-1H-imidazol-2-yl]-4-methoxy-7-morpholin-4-yl-benzothiazole as yellow solid; M.p.: 235–237° C.; MS (ISP): m/e=451 (M+H$^+$).

EXAMPLE 17

2-(5-Benzo[b]thiophen-3-yl-1H-imidazol-2-yl)-4-methoxy-7-morpholin-4-yl-benzothiazole 0.30 g 4-Methoxy-7-morpholin-4-yl-benzothiazole-2-carboxylic acid and 0.19 g 1,1'-carbonyl-diimidazole in 6 ml DMF were stirred at room temperature for 4 hours. 0.26 g 2-amino-1-benzo[b]thiophen-3-yl-ethanone hydrochloride and 0.–16 ml triethylamine were added and stirring was continued for two days at room temperature. 100 ml water was added and the mixture was extracted with ethylacetate. The precipitate was filtered to yield 0.21 g (44%) 4-methoxy-7-morpholin-4-yl-benzothiazole-2-carboxylic acid (2-benzo[b]thiophen-3-yl-2-oxo-ethyl)-amide as a yellow solid; M.p.: 256–258° C.; MS (ISP): m/e=468 (M+H$^+$).

A mixture of 0.15 g 4-methoxy-7-morpholin-4-yl-benzothiazole-2-carboxylic acid (2-benzo[b]thiophen-3-yl-2-oxo-ethyl)-amide and 0.43 g ammonium triflouroacetate was melted at 210° C. for 30 minutes and, after cooling to room temperature, suspended in water. Extraction with dichloromethane and chromatography on silicagel with ethylacetate/hexane 1:1 gave 0.10 g (69%) 2-(5-benzo[b]thiophen-3-yl-1H-imidazol-2-yl)-4-methoxy-7-morpholin-4-yl-benzothiazole as yellow solid; M.p.: 161–162° C.; MS (ISP): m/e=449 (M+H$^+$).

EXAMPLE 18

4-Methoxy-7-morpholin-4-yl-2-(4-thiophen-2-yl-1H-imidazol-2-yl)-benzothiazole 0.40 g 4-Methoxy-7-morpholin-4-yl-benzothiazole-2-carboxylic acid and 0.25 g 1,1'-carbonyl-diimidazole in 40 ml DMF were stirred at room temperature for 1.5 hours. 0.27 g 2-amino-1-(2-thienyl)ethanone hydrochloride and 0.15 g triethylamine were added and stirring was continued over night at room temperature. 350 ml water was added and the mixture was extracted with ethylacetate. Chromatography on silicagel with ethylacetate/hexane 4:6 yielded 0.25 g (43%) 4-methoxy-7-morpholin-4-yl-benzothiazole-2-carboxylic acid (2-oxo-2-thiophen-2-yl-ethyl)-amide as a yellow solid; MS (ISP): m/e=418 (M+H$^+$).

A mixture of 0.10 g 4-methoxy-7-morpholin-4-yl-benzothiazole-2-carboxylic acid (2-oxo-2-thiophen-2-yl-ethyl)-amide and 0.32 g ammonium triflouroacetate was melted at 165° C. for 60 minutes and, after cooling to room temperature, suspended in water. Extraction with dichloromethane and chromatography on silicagel with ethylacetate/hexane 1:1 gave 0.02 g (25%) 4-methoxy-7-morpholin-4-yl-2-(4-thiophen-2-yl-1H-imidazol-2-yl)-benzothiazole as yellow solid; MS (ISP): m/e=399 (M+H$^+$).

EXAMPLE 19

4-Methoxy-7-morpholin-4-yl-2-(4-thiophen-3-yl-1H-imidazol-2-yl)-benzothiazole 0.40 g 4-Methoxy-7-morpholin-4-yl-benzothiazole-2-carboxylic acid and 0.25 g 1,1'-carbonyl-diimidazole in 40 ml DMF were stirred at room temperature for 1.5 hours. 0.27 g 2-amino-1-(2-thienyl)ethanone hydrochloride and 0.15 g triethylamine were added and stirring was continued over night at room temperature. 350 ml water was added and the mixture was extracted with ethylacetate. Chromatography on silicagel with ethylacetate/hexane 4:6 yielded 0.20 g (35%) 4-methoxy-7-morpholin-4-yl-benzothiazole-2-carboxylic acid (2-oxo-2-thiophen-3-yl-ethyl)-amide as a yellow solid; MS (ISP): m/e=418 (M+H$^+$).

A mixture of 0.10 g 4-methoxy-7-morpholin-4-yl-benzothiazole-2-carboxylic acid (2-oxo-2-thiophen-3-yl-ethyl)-amide and 0.32 g ammonium triflouroacetate was melted at 170° C. for 50 minutes and, after cooling to room temperature, suspended in water. Extraction with dichloromethane and chromatography on silicagel with ethylacetate/hexane 1:1 gave 0.06 g (59%) 4-methoxy-7-morpholin-4-yl-2-(4-thiophen-3-yl-1H-imidazol-2-yl)-benzothiazole as yellow solid; MS (ISP): m/e=399 (M+H$^+$).

EXAMPLE 20

4-Methoxy-2-[5-(3-methyl-benzo[b]thiophen-2-yl)-1H-imidazol-2-yl]-7-morpholin-4-yl-benzothiazole 1.11 g 2-Bromoacetyl-3-methyl-benzothiophene and 0.56 g hexamethylenetetramine in 20 ml trichloromethane were stirred at room temperature for 16 hours. After addition of 15 ml diethylether the mixture was filtered. The solid residue was stirred at room temperature for 3 hours in a mixture of 15 ml methanol and 1.9 ml concentrated hydrochloric acid. The solvents were distilled off and the residue recrystallized from water to yield 0.90 g (93%) 2-amino-1-(3-methyl-benzo[b]thiophen-2-yl)-ethanone hydrochloride as off-white solid; MS (El): m/e=205 (M$^+$, 40%), 175 (M-CH$_2$NH$_2$, 100%), 147 (M-COCH$_2$NH$_2$, 20%).

0.30 g 4-Methoxy-7-morpholin-4-yl-benzothiazole-2-carboxylic acid and 0.19 g 1,1'-carbonyl-diimidazole in 18 ml DMF were stirred at room temperature for 4 hours. 0.27 g 2-amino-1-(3-methyl-benzo[b]thiophen-2-yl)-ethanone hydrochloride and 0.16 ml triethylamine were added and stirring was continued for two days at room temperature.

Water was added and the mixture was extracted with ethylacetate. Chromatography on silicagel with ethylacetate/hexane 4:6 yielded 0.12 g (23%) 4-methoxy-7-morpholin-4-yl-benzothiazole-2-carboxylic acid [2-(3-methyl-benzo[b]thiophen-2-yl)-2-oxo-ethyl]-amide as a yellow solid; M.p.: 186–187° C.; MS (ISP): m/e=482 (M+H⁺).

A mixture of 0.16 g 4-methoxy-7-morpholin-4-yl-benzothiazole-2-carboxylic acid [2-(3-methyl-benzo[b]thiophen-2-yl)-2-oxo-ethyl]-amide and 0.44 g ammonium triflouroacetate was melted at 180° C. for 45 minutes and, after cooling to room temperature, suspended in water. Extraction with dichloromethane and chromatography on silicagel with ethylacetate/hexane 1:1 gave 0.08 g (51%) 4-methoxy-2-[5-(3-methyl-benzo[b]thiophen-2-yl)-1H-imidazol-2-yl]-7-morpholin-4-yl-benzothiazole as yellow solid; M.p.: 213–215° C.; MS (ISP): m/e=463 (M+H⁺).

EXAMPLE 21

4-Methoxy-7-morpholin-4-yl-2-(4-thiophen-2-ylmethyl-1H-imidazol-2-yl)-benzothiazole 19.6 g 2-Thiopheneacetic acid and 24.8 g 1,1'-carbonyldiimidazole in 150 ml DMF were stirred at 0–4° C. for 4 hours. 14.2 ml methyl isocyanoacatate were added and stirring was continued over night at room temperature. Water was added and the mixture was extracted with ethylacetate. Chromatography on silicagel with ethylacetate/hexane 4:6 yielded 2.01 g (7%) 5-thiophen-2-ylmethyl-oxazole-4-carboxylic acid methyl ester as a yellow solid; MS (EI): m/e=223 (M⁺16%), 191 (M-CH₂OH, 100%), 163 (10%), 136 (20%).

2.23 g 5-Thiophen-2-ylmethyl-oxazole-4-carboxylic acid methyl ester were suspended in 80 ml 6 N hydrochloric acid and stirred for 5 hours at 95° C. The solvent was removed at 30° C. under vacuum and the residue was suspended in ethylacetate, filtered and dried to yield 1.52 g (79%) 1-amino-3-thiophen-2-yl-propan-2-one hydrochloride; MS (ISP): m/e=156 (M+H⁺).

0.41 g 4-Methoxy-7-morpholin-4-yl-benzothiazole-2-carboxylic acid and 0.14 g 1,1'-carbonyl-diimidazole in 11 ml DMF were stirred at room temperature for 16 hours. 0.16 g 1-amino-3-thiophen-2-yl-propan-2-one hydrochloride and 0.23 ml triethylamine were added and stirring was continued for two days at room temperature. Water was added and the mixture was extracted with ethylacetate. Chromatography on silicagel with ethylacetate/hexane 3:7–7:3 to yielded 0.06 g (18%) 4-methoxy-7-morpholin-4-yl-benzothiazole-2-carboxylic acid (2-oxo-3-thiophen-2-yl-propyl)-amide as a yellow solid; MS (ISP): m/e=432 (M+H⁺).

A mixture of 0.04 g 4-methoxy-7-morpholin-4-yl-benzothiazole-2-carboxylic acid (2-oxo-3-thiophen-2-yl-propyl)-amide and 0.13 g ammonium triflouroacetate was melted at 165° C. for 60 minutes and, after cooling to room temperature, suspended in water. Extraction with dichloromethane and chromatography on silicagel with ethylacetate/hexane 1:1 gave 0.005 g (13%) 4-methoxy-7-morpholin-4-yl-2-(4-thiophen-2-ylmethyl-1H-imidazol-2-yl)-benzothiazole as yellow solid; MS (ISP): m/e=413 (M+H⁺).

EXAMPLE 22

4-Methoxy-7-morpholin-4-yl-2-(4,5,6,7-tetrahydro-1H-benzoimidazol-2-yl)-benzothiazole 6.00 g 4-Methoxy-7-morpholin-4-yl-benzothiazole-2-carboxylic acid and 3.75 g 1,1'-carbonyl-diimidazole in 360 ml dimethylformamide were stirred at room temperature for 16 hours. 3.36 g 2-amino-cyclohexanone hydrochloride and 3.14 ml triethylamine were added and stirring was continued over night at room temperature. Water was added and the mixture was extracted with ethylacetate. Chromatography on silicagel with ethylacetate/hexane 1:1 to yielded 0.16 g (2%) 4-methoxy-7-morpholin-4-yl-benzothiazole-2-carboxylic acid (2-oxo-cyclohexyl)-amide as a yellow solid; M.p.: 195–197° C.; MS (ISP): m/e=390 (M+H⁺).

A mixture of 0.10 g 4-methoxy-7-morpholin-4-yl-benzothiazole-2-carboxylic acid (2-oxo-cyclohexyl)-amide and 0.34 g ammonium triflouroacetate was melted at 165° C. for 50 minutes and, after cooling to room temperature, suspended in water. Extraction with dichloromethane and chromatography on silicagel with ethylacetate/hexane 6:4 gave 0.04 g (39%) 4-methoxy-7-morpholin-4-yl-2-(4,5,6,7-tetrahydro-1H-benzoimidazol-2-yl)-benzothiazole as light brown solid; MS (ISP): m/e=371 (M+H⁺).

EXAMPLE 23

2-(4-Methoxy-7-morpholin-4-yl-benzothiazol-2-yl)-3,4,6,7-tetrahydro-pyrano[3,4-d]imidazole 139 ml (1015 mmol) Diethyl oxalate was heated to 120° C. 30.3 g (145 mmol) 2-methoxy-5-morpholin-4-yl-phenylamine was added very cautiously in small quantities and the mixture was heated for 90 minutes at 180° C. After cooling to room temperature and filtration 1.5 n-hexane were added. The resulting precipitate was collected by filtration. After washing with hexane and drying, 34.4 g (77%) N-(2-methoxy-5-morpholin-4-yl-phenyl)-oxalamic acid ethyl ester was obtained as greenish crystals, M.p.: 95–97° C., MS m/e (%): 309 (M+H⁺, 100).

To 33.9 g (110 mmol) N-(2-methoxy-5-morpholin-4-yl-phenyl)-oxalamic acid ethyl ester in 652 ml boiling xylene was added 8.80 g (40 mmol) phosphorus pentasulfide in small portions over a period of 30 minutes. The mixture was refluxed for 5 hours, cooled to room temperature and filtered. The solution was extracted 7 times with 100 ml 1N NaOH. The aqueous phase was washed twice with 100 ml toluene, filtered, and treated at 0–5° C. with concentrated hydrochloric acid until pH 1 was reached. Filtration of the precipitate yielded 20.2 g (62%) (2-methoxy-5-morpholin-4-yl-phenylamino)-thioxo-acetic acid as yellow crystals with M.p.: 156–158° C., MS m/e (%): 297 (M+H⁺, 100).

A solution of 10.5 g (35.4 mmol) (2-methoxy-5-morpholin-4-yl-phenylamino)-thioxo-acetic acid in 248 ml (248 mmol) 1N NaOH was added dropwise to a solution of 40.1 g (119 mmol) potassium ferricyanide in 119 ml water at a rate that the temperature did not exceed 10° C. The mixture was stirred for 3 hours at 10° C. and concentrated hydrochloric acid was added until pH 1 was reached. Filtration of the precipitate and drying yielded 8.80 g (84%) 4-methoxy-7-morpholin-4-yl-benzothiazole-2-carboxylic acid as yellow crystals with M.p.: 99–100° C., MS m/e (%): 295 (M+H⁺, 100).

A suspension of 3.51 g 4-methoxy-7-morpholin-4-yl-benzothiazole-2-carboxylic acid and 1.78 g 1,1'-carbonyl-diimidazol in 30 ml DMF was stirred at room temperature for 18 hours. 0.8 ml Ammonium hydroxide (25% in water) was added and stirring was continued for 5 hours. Extraction with water/ethylacetate and crystallization from dichloromethane yielded 1.17 g (40%) 4-methoxy-7-morpholin-4-yl-benzothiazole-2-carboxylic acid amide as a yellow solid; M.p.: 228–231° C.; MS (ISP): m/e=294 (M+H⁺). To a solution of 4.67 g 4-methoxy-7-morpholin-4-yl-benzothiazole-2-carboxylic acid amide and 2.18 g imidazole in 95 ml pyridine were added at 0° C. 5.95 ml phosphoroxychloride. After 5 hours the cold solution was diluted with ethylacetate and extracted with water. The organic solution was dried with sodiumsulfate and the solvents were distilled off to yield 3.94 g 4-methoxy-7-morpholin-4-yl-benzothiazole-2-carbonitrile as yellow solid; M.p.: 145–147° C.; MS (ISP): m/e=276 (M+H$^+$).

0.50 g 4-Methoxy-7-morpholin-4-yl-benzothiazole-2-carbonitrile and 5.46 ml triethylamine in 13 ml pyridine were stirred for 4 hours with about 5 ml hydrogen sulfide at room temperature. Solvent and excess hydrogen sulfide were removed and the residue chromatographed on siligagel with ethylacetate/heptane 1:1 to yield 0.49 g (87%) 4-methoxy-7-morpholin-4-yl-benzothiazole-2-carbothioic acid amide; M.p.: 238° C.; MS (ISP): m/e=310 (M+H$^+$).

0.56 g 4-Methoxy-7-morpholin-4-yl-benzothiazole-2-carbothioic acid amide in 56 ml tetrahydrofurane were reacted with 11.3 ml iodomethane at 50° C. for 4 hours. All volatile components were distilled off under vacuum and the residue was dissolved in a solution of 1.03 g 4,4-diethoxy-tetrahydro-pyran-3-ylamine in 60 ml tetrahydrofurane. The mixture was stirred at 50° C. overnight, the solvent was distilled off and the residue was suspended in 98 ml hydrochloric acid (~20%) and stirred for 3 hours at room temperature. Extraction with dichloromethane and a second extraction after pH adjustment to pH=8 followed by chromatography on silicagel with dichloromethane/methanol 95:5 and then on aluminium oxide with dichloromethane/methanol 98:2 yielded 0.06 g (9%) 2-(4-methoxy-7-morpholin-4-yl-benzothiazol-2-yl)-3,4,6,7-tetrahydro-pyrano[3,4-d]imidazole; M.p.: 203–204° C.; MS (ISP): m/e=373 (M+H$^+$).

EXAMPLE 24

2-(4-Methoxy-7-morpholin-4-yl-benzothiazol-2-yl)-4,5,7,8-tetrahydro-1H-imidazo[4,5-d]azepine-6-carboxylic acid tert-butyl ester To a stirred solution of 16.4 g 2,3,6,7-tetrahydro-azepine-1-carboxylic acid tert-butyl ester in 420 ml dichloromethane was added at −60° C. 35.8 g m-chloroperbenzoic acid (70% purity). The mixture was allowed to slowly warm to room temperature overnight, 1 l ethylacetate was added and the solution was extracted with aqueous sodium bicarbonate, 1N aqueous sodium hydroxide and brine. Evaporation of the solvent and chromatography yielded 14.5 g (82%) 8-oxa-4-aza-bicyclo[5.1.0]octane-4-carboxylic acid tert-butyl ester as colorless liquid; MS (EI): m/e=213 (M$^+$,5%), 158 (22%), 140 (12%), 57 (100%). To a solution of 14.3 g 8-oxa-4-aza-bicyclo[5.1.0]octane-4-carboxylic acid tert-butyl ester in 750 ethanol was added 150 ml water, 35.8 g ammonium chloride and 43.6 g sodium azide. The mixture was stirred at 75° C. over night, the solvents were greatly removed by distillation under vacuum and the residue was suspended in ethanol and filtered. The ethanol was distilled off and the residue was suspended in ethylacetate and filtered. Removal of the solvent and chromatography on silicagel with ethylacetate/hexane 1:1, yielded 13.5 g (79%) 4-azido-5-hydroxy-azepane-1-carboxylic acid tert-butyl ester as a viscous oil; MS (ISP): m/e=257 (M+H$^+$).

6.54 g 4-Azido-5-hydroxy-azepane-1-carboxylic acid tert-butyl ester in 51 ml methanol were hydrogenated in the presence of 0.6 g palladium on charcoal (10%) to yield 5.85 g (quant.) 4-amino-5-hydroxy-azepane-1-carboxylic acid tert-butyl ester as viscous oil; MS (ISP): m/e=231 (M+H$^+$).

0.50 g 4-Methoxy-7-morpholin-4-yl-benzothiazole-2-carboxylic acid and 0.31 g 1,1'-carbonyl-diimidazole in 25 ml dimethylformamide were stirred at room temperature for 16 hours. 0.43 g 4-amino-5-hydroxy-azepane-1-carboxylic acid tert-butyl ester were added and stirring was continued for 16 hours at room temperature. Water was added and the mixture was extracted with ethylacetate. Chromatography on silicagel with dichloromethane/methanol 98:2 yielded 0.68 g (79%) 4-hydroxy-5-[(4-methoxy-7-morpholin-4-yl-benzothiazole-2-carbonyl)-amino]-azepane-1-carboxylic acid tert-butyl ester as a yellow solid; M.p.: 71–73° C.; MS (ISP): m/e=507 (M+H$^+$).

To a solution of 0.56 g 4-hydroxy-5-[(4-methoxy-7-morpholin-4-yl-benzothiazole-2-carbonyl)-amino]-azepane-1-carboxylic acid tert-butyl ester in 10 ml dimethylsulfoxide were added 0.93 ml triethylamine, 10 ml dichlotomethane and a solution of 0.58 g sulfur trioxide pyridine complex in 8 ml dimethylsulfoxide. The mixture was stirred for 18 hours at room temperature. Extraction with water/ ethylacetate and chromatography on silicagel with dichloromethane/methanol 97:3 yielded 0.49 g (87%) 4-[(4-methoxy-7-morpholin-4-yl-benzothiazole-2-carbonyl)-amino]-5-oxo-azepane-1-carboxylic acid tert-butyl ester as yellow solid; M.p.: 95–97° C.; MS (ISP): m/e=505 (M+H$^+$).

A mixture of 0.15 g 4-[(4-methoxy-7-morpholin-4-yl-benzothiazole-2-carbonyl)-amino]-5-oxo-azepane-1-carboxylic acid tert-butyl ester and 0.46 g ammonium acetate was melted at 120° C. for 3 hours and, after cooling to room temperature, suspended in a 1:1 mixture of water and saturated aqueous sodiumbicarbonate. Extraction with dichloromethane and chromatography on silicagel with dichloromethane/methanol 98:2 gave 0.10 g (72%) 2-(4-methoxy-7-morpholin-4-yl-benzothiazol-2-yl)-4,5,7,8-tetrahydro-1H-imidazo[4,5-d]azepine-6-carboxylic acid tert-butyl ester as yellow solid; M.p.: 142–144° C.; MS (ISP): m/e=486 (M+H$^+$).

EXAMPLE 25

2-(4-Methoxy-7-morpholin-4-yl-benzothiazol-2-yl)-1,4,5,6,7,8-hexahydro-imidazo[4,5-d]azepine hydrochloride 1.70 g 2-(4-Methoxy-7-morpholin-4-yl-benzothiazol-2-yl)-4,5,7,8-tetrahydro-1H-imidazo[4,5-d]azepine-6-carboxylic acid tert-butyl ester were dissolved in 130 ml of a 7.7 molar solution of hydrogen chloride in methanol. After stirring at room temperature the solvent was distilled off and the residue was recrystallized from ethanol to yield 1.01 g (68%) 2-(4-methoxy-7-morpholin-4-yl-benzothiazol-2-yl)-1,4,5,6,7,8-hexahydro-imidazo[4,5-d]azepine hydrochloride as yellow solid; M.p.: 267–269° C.; MS (ISP): m/e=386 (M+H$^+$).

EXAMPLE 26

(4-Fluoro-phenyl)-[2-(4-methoxy-7-morpholin-4-yl-benzothiazol-2-yl)-4,5,7,8-tetrahydro-1H-imidazo[4,5-d]azepin-6-yl]-methanone To a suspension of 0.037 g 2-(4-methoxy-7-morpholin-4-yl-benzothiazol-2-yl)-1,4,5,6,7,8-hexahydro-imidazo[4,5-d]azepine hydrochloride in 3 ml tetrahydrofurane were added at 0–4° C. 0.06 ml N-ethyldiisopropylamine and 0.01 μl 4-fluorobenzoylchloride. The mixture was refluxed for 17 hours, silicagel was added and the solvent was distilled off. The residue was transferred to a column prefilled with silicagel and was chromatographed with dichloromethane/methanol 96:4 to yield 0.022 g (49%) (4-fluoro-phenyl)-[2-(4-methoxy-7-morpholin-4-yl-benzothiazol-2-yl)-4,5,7,8-tetrahydro-1H-imidazo[4,5-d]azepin-6-yl]-methanone as yellow solid; M.p.: 205–207° C.; MS (ISP): m/e=506 (M–H$^+$).

EXAMPLE 27

1-[2-(4-Methoxy-7-morpholin-4-yl-benzothiazol-2-yl)-4,5,7,8-tetrahydro-1H-imidazo[4,5-d]azepin-6-yl]-ethanone To a suspension of 0.037 g 2-(4-methoxy-7-morpholin-4-yl-benzothiazol-2-yl)-1,4,5,6,7,8-hexahydro-imidazo[4,5-d]azepine hydrochloride in 3 ml tetrahydrofurane were added at 0–4° C. 0.06 ml N-ethyldiisopropylamine and 0.007 ml acetylchloride. The mixture was refluxed for 17 hours, silicagel was added and the solvent was distilled off. The residue was transferred to a column prefilled with silicagel and was chromatographed with dichloromethane/methanol 96:4 to yield 0.028 g (74%) 1-[2-(4-methoxy-7-morpholin-4-yl-benzothiazol-2-yl)-4,5,7,8-tetrahydro-1H-imidazo[4,5-d]azepin-6-yl]-ethanone as yellow solid; M.p.: 195–197° C.; MS (ISP): m/e=428 (M+H$^+$).

EXAMPLE 28

[2-(4-Methoxy-7-morpholin-4-yl-benzothiazol-2-yl)-4,5,7,8-tetrahydro-1H-imidazo[4,5-d]azepin-6-yl]-o-tolyl-methanone To a suspension of 0.04 g 2-(4-methoxy-7-morpholin-4-yl-benzothiazol-2-yl)-1,4,5,6,7,8-hexahydro-imidazo[4,5-d]azepine hydrochloride in 3.4 ml tetrahydrofurane were added at 0–4° C. 0.07 ml N-ethyldiisopropylamine and 0.017 g o-toluoyl chloride. The mixture was refluxed for 17 hours, silicagel was added and the solvent was distilled off. The residue was transferred to a column prefilled with silicagel and was chromatographed with dichloromethane/methanol 96:4 to yield 0.047 g (94%) [2-(4-methoxy-7-morpholin-4-yl-benzothiazol-2-yl)-4,5,7,8-tetrahydro-1H-imidazo[4,5-d]azepin-6-yl]-o-tolyl-methanone as yellow solid; M.p.: 194–196° C.; MS (ISP): m/e=504 (M+H$^+$).

EXAMPLE 29

1-[2-(4-Methoxy-7-morpholin-4-yl-benzothiazol-2-yl)-4,5,7,8-tetrahydro-1H-imidazo[4,5-d]azepin-6-yl]-2,2-dimethyl-propan-1-one To a suspension of 0.04 g 2-(4-methoxy-7-morpholin-4-yl-benzothiazol-2-yl)-1,4,5,6,7,8-hexahydro-imidazo[4,5-d]azepine hydrochloride in 3.4 ml tetrahydrofurane were added at 0–4° C. 0.07 ml N-ethyldiisopropylamine and 0.014 g pivaloyl chloride. The mixture was refluxed for 17 hours, silicagel was added and the solvent was distilled off. The residue was transferred to a column prefilled with silicagel and was chromatographed with dichloromethane/methanol 96:4 to yield 0.047 g (88%) 1-[2-(4-methoxy-7-morpholin-4-yl-benzothiazol-2-yl)-4,5,7,8-tetrahydro-1H-imidazo[4,5-d]azepin-6-yl]-2,2-dimethyl-propan-1-one as yellow solid; MS (ISP): m/e=470 (M+H$^+$).

EXAMPLE 30

Cyclopropyl-[2-(4-methoxy-7-morpholin-4-yl-benzothiazol-2-yl)-4,5,7,8-tetrahydro-1H-imidazo[4,5-d]azepin-6-yl]-methanone To a suspension of 0.04 g 2-(4-methoxy-7-morpholin-4-yl-benzothiazol-2-yl)-1,4,5,6,7,8-hexahydro-imidazo[4,5-d]azepine hydrochloride in 3.4 ml tetrahydrofurane were added at 0–4° C. 0.07 ml N-ethyldiisopropylamine and 0.012 g cyclopropanecarbonyl chloride. The mixture was refluxed for 17 hours, silicagel was added and the solvent was distilled off. The residue was transferred to a column prefilled with silicagel and was chromatographed with dichloromethane/methanol 96:4 to yield 0.04 g (90%) cyclopropyl-[2-(4-methoxy-7-morpholin-4-yl-benzothiazol-2-yl)-4,5,7,8-tetrahydro-1H-imidazo[4,5-d]azepin-6-yl]-methanone as yellow solid; MS (ISP): m/e=454 (M+H$^+$).

EXAMPLE 31

2-(4-Methoxy-7-morpholin-4-yl-benzothiazol-2-yl)-4,5,7,8-tetrahydro-1H-imidazo[4,5-d]azepine-6-carboxylic acid dimethylamide To a suspension of 0.04 g 2-(4-methoxy-7-morpholin-4-yl-benzothiazol-2-yl)-1,4,5,6,7,8-hexahydro-imidazo[4,5-d]azepine hydrochloride in 3.4 ml tetrahydrofurane were added at 0–4° C. 0.07 ml N-ethyldiisopropylamine and 0.012 g dimethylcarbamoyl chloride. The mixture was refluxed for 17 hours, silicagel was added and the solvent was distilled off. The residue was transferred to a column prefilled with silicagel and was chromatographed with dichloromethane/methanol 96:4 to yield 0.04 g (92%) 2-(4-methoxy-7-morpholin-4-yl-benzothiazol-2-yl)-4,5,7,8-tetrahydro-1H-imidazo[4,5-d]azepine-6-carboxylic acid dimethylamide as yellow solid; MS (ISP): m/e=457 (M+H$^+$).

EXAMPLE 32

2-Methoxy-1-[2-(4-methoxy-7-morpholin-4-yl-benzothiazol-2-yl)-4,5,7,8-tetrahydro-1H-imidazo[4,5-d]azepin-6-yl]-ethanone To a suspension of 0.13 g 2-(4-methoxy-7-morpholin-4-yl-benzothiazol-2-yl)-1,4,5,6,7,8-hexahydro-imidazo[4,5-d]azepine hydrochloride in 10 ml tetrahydrofurane were added at 0–4° C. 0.21 ml N-ethyldiisopropylamine and 0.037 g methoxyacetyl chloride. The mixture was refluxed for 17 hours, silicagel was added and the solvent was distilled off. The residue was transferred to a column prefilled with silicagel and was chromatographed with dichloromethane/methanol 96:4 to yield 0.126 g (91%) 2-methoxy-1-[2-(4-methoxy-7-morpholin-4-yl-benzothiazol-2-yl)-4,5,7,8-tetrahydro-1H-imidazo[4,5-d]azepin-6-yl]-ethanone as yellow solid; MS (ISP): m/e=458 (M+H$^+$).

EXAMPLE 33

2-(4-Methoxy-7-morpholin-4-yl-benzothiazol-2-yl)-4,5,7,8-tetrahydro-1H-imidazo[4,5-d]azepine-6-carboxylic acid ethyl ester To a suspension of 0.04 g 2-(4-methoxy-7-morpholin-4-yl-benzothiazol-2-yl)-1,4,5,6,7,8-hexahydro-imidazo[4,5-d]azepine hydrochloride in 3.4 ml tetrahydrofurane were added at 0–4° C. 0.07 ml N-ethyldiisopropylamine and 0.011 g ethylchloroformate. The mixture was refluxed for 17 hours, silicagel was added and the solvent was distilled off. The residue was transferred to a column prefilled with silicagel and was chromatographed with dichloromethane/methanol 96:4 to yield 0.028 g (62%) 2-(4-methoxy-7-morpholin-4-yl-benzothiazol-2-yl)-4,5,7,8-tetrahydro-1H-imidazo[4,5-d]azepine-6-carboxylic acid ethyl ester as yellow solid; MS (ISP): m/e=458 (M+H$^+$).

EXAMPLE 34

6-Methanesulfonyl-2-(4-methoxy-7-morpholin-4-yl-benzothiazol-2-yl)-1,4,5,6,7,8-hexahydro-imidazo[4,5-d]azepine To a suspension of 0.04 g 2-(4-methoxy-7-morpholin-4-yl-benzothiazol-2-yl)-1,4,5,6,7,8-hexahydro-imidazo[4,5-d]azepine hydrochloride in 3.4 ml tetrahydrofurane were added at 0–4° C. 0.07 ml N-ethyldiisopropylamine and 0.009 ml methanesulfonyl chloride. The mixture was refluxed for 17 hours, silicagel was added and the solvent was distilled off. The residue was transferred to a column prefilled with silicagel and was chromatographed with dichloromethane/methanol 96:4 to yield 0.015 g (32%) 6-methanesulfonyl-2-(4-methoxy-7-morpholin-4-yl-benzothiazol-2-yl)-1,4,5,6,7,8-hexahydro-imidazo[4,5-d]azepine as yellow solid; MS (ISP): m/e=464 (M+H$^+$).

EXAMPLE 35

6-(2-Methoxy-ethyl)-2-(4-methoxy-7-morpholin-4-yl-benzothiazol-2-yl)-1,4,5,6,7,8-hexahydro-imidazo[4,5-d]azepine 0.09 g 2-Methoxy-1-[2-(4-methoxy-7-morpholin-4-yl-benzothiazol-2-yl)-4,5,7,8-tetrahydro-1H-imidazo[4,5-d]azepin-6-yl]-ethanone in 5 ml tetrahydrofurane were reacted with 0.2 ml lithiumaluminium hydride solution (1 M in tetrahydrofurane) over night at room temperature. 5 ml ethylacetate was added followed by 5 ml water at 0–5° C. Extraction with ethylacetate and chromatography on silicagel with dichloromethane/methanol 96:4 yielded 0.047 g (53%) 6-(2-methoxy-ethyl)-2-(4-methoxy-7-morpholin-4-yl-benzothiazol-2-yl)-1,4,5,6,7,8-hexahydro-imidazo[4,5-d]azepine as yellow solid; MS (ISP): m/e=444 (M+H$^+$).

EXAMPLE 36

2-(4-Methoxy-7-morpholin-4-yl-benzothiazol-2-yl)-3,4,6,7-tetrahydro-imidazo[4,5-c]pyridine-5-carboxylic acid tert-butyl ester g 4-Methoxy-7-morpholin-4-yl-benzothiazole-2-carbothioic acid amide and 20.3 ml iodomethane in 100 ml tetrahydrofurane were stirred at room temperature for three days. The resulting precipitate was filtered to yield 0.74 g (51%) 4-methoxy-7-morpholin-4-yl-benzothiazole-2-carboximidothioic acid methyl ester hydroiodide; M.p.: 169–171° C.; MS (ISP): m/e=324 (M+H$^+$).

To a suspension of 0.50 g 4-methoxy-7-morpholin-4-yl-benzothiazole-2-carboximidothioic acid methyl ester hydroiodide in 33 ml tetrahydrofurane was added 1.34 g 3-amino-4,4-diethoxy-piperidine-1-carboxylic acid tert-butyl ester and the mixture was stirred at room temperature for two days. Then 0.2 ml boron trifluoride etherate was added and the solvent was distilled off under vacuum. Again 0.2 ml boron trifluoride etherate was added and the mixture was dissolved in 30 ml dimethylformamide and heated for 10 minutes at 125° C. The solvent was distilled off and the residue was dissolved in dichloromethane and extracted with water. The organic layer was dried with sodium sulfate, filtered and the solvent was evaporated. Chromatography on silicagel with ethylacatate/hexane 1:1 followed by chromatography on aluminiumoxide with ethylacatate/hexane 1:1 yielded 0.18 g (35%) 2-(4-methoxy-7-morpholin-4-yl-benzothiazol-2-yl)-3,4,6,7-tetrahydro-imidazo[4,5-c]pyridine-5-carboxylic acid tert-butyl ester as an amorphous solid; m/e=472 (M+H$^+$).

EXAMPLE 37

2-(4-Methoxy-7-morpholin-4-yl-benzothiazol-2-yl)-4,5,6,7-tetrahydro-1H-imidazo[4,5-c]pyridine; hydrochloride 0.08 g 2-(4-Methoxy-7-morpholin-4-yl-benzothiazol-2-yl)-3,4,6,7-tetrahydro-imidazo[4,5-c]pyridine-5-carboxylic acid tert-butyl ester was dissolved in 13 ml of a 7.7 molar solution of hydrogen chloride in methanol. After stirring at room temperature for 2 days the solvent was distilled off, toluene was added and distilled off and the residue was suspended in ethanol and filtered to yield 0.056 g (81%) 2-(4-methoxy-7-morpholin-4-yl-benzothiazol-2-yl)-4,5,6,7-tetrahydro-1H-imidazo[4,5-c]pyridine hydrochloride as yellow solid; M.p.: 268–271° C.; MS (ISP): m/e=372 (M+H$^+$).

EXAMPLE 38

[2-(4-Methoxy-7-morpholin-4-yl-benzothiazol-2-yl)-1,4,6,7-tetrahydro-imidazo[4,5-c]pyridin-5-yl]-o-tolyl-methanone To a suspension of 0.01 g 2-(4-methoxy-7-morpholin-4-yl-benzothiazol-2-yl)-4,5,6,7-tetrahydro-1H-imidazo[4,5-c]pyridine hydrochloride in 0.8 ml tetrahydrofurane were added at 0–4° C. 0.02 ml N-ethyldiisopropylamine and 0.004 ml o-toluoyl chloride. The mixture was refluxed over night, silicagel was added and the solvent was distilled off. The residue was transferred to a column prefilled with silicagel and was chromatographed with ethylacetate/methanol 98:2 to yield 0.006 g (50%)[2-(4-methoxy-7-morpholin-4-yl-benzothiazol-2-yl)-1,4,6,7-tetrahydro-imidazo[4,5-c]pyridin-5-yl]-o-tolyl-methanone as yellow solid; MS (ISP): m/e=490 (M+H$^+$).

EXAMPLE 39

1-[2-(4-Methoxy-7-morpholin-4-yl-benzothiazol-2-yl)-1,4,6,7-tetrahydro-imidazo[4,5-c]pyridin-5-yl]-ethanone To a suspension of 0.01 g 2-(4-methoxy-7-morpholin-4-yl-benzothiazol-2-yl)-4,5,6,7-tetrahydro-1H-imidazo[4,5-c]pyridine hydrochloride in 0.8 ml tetrahydrofurane were added at 0–4° C. 0.02 ml N-ethyldiisopropylamine and 0.002 ml acetyl chloride in 0.25 ml tetrahydrofurane. The mixture was refluxed over night, silicagel was added and the solvent was distilled off. The residue was transferred to a column prefilled with silicagel and was chromatographed with ethylacetate/methanol 95:5 to yield 0.009 g (89%) 1-[2-(4-methoxy-7-morpholin-4-yl-benzothiazol-2-yl)-1,4,6,7-tetrahydro-imidazo[4,5-c]pyridin-5-yl]-ethanone as yellow solid; M.p.: 155–157° C.; MS (ISP): m/e=414 (M+H$^+$).

EXAMPLE 40

2-(4-Methoxy-7-morpholin-4-yl-benzothiazol-2-yl)-1,4,6,7-tetrahydro-imidazo[4,5-c]pyridine-5-carboxylic acid ethyl ester To a suspension of 0.01 g 2-(4-methoxy-7-morpholin-4-yl-benzothiazol-2-yl)-4,5,6,7-tetrahydro-1H-imidazo[4,5-c]pyridine hydrochloride in 0.8 ml tetrahydrofurane were added at 0–4° C. 0.06 ml N-ethyldiisopropylamine and 0.003 ml ethyl chloroformate in 0.26 ml tetrahydrofurane. The mixture was refluxed over night, additional 0.06 ml N-ethyldiisopropylamine and 0.05 ml ethyl chloroformate were added and heating was continued for 4 hours. 0.015 ml benzylamine were added and the mixture was kept at 80° C. for 1 hour. Silicagel was added and the solvent was distilled off. The residue was transferred to a column prefilled with silicagel and was chromatographed with ethylacetate. A second chromatography first with ethylacetate/hexane 1:1 and then with ethylacetate/methanol 9:1 yielded 0.003 g (25%) 2-(4-methoxy-7-morpholin-4-yl-benzothiazol-2-yl)-1,4,6,7-tetrahydro-imidazo[4,5-c]pyridine-5-carboxylic acid ethyl ester as yellow solid; MS (ISP): m/e=444 (M+H$^+$).

EXAMPLE 41

(2-Chloromethyl-pyridin-4-yl)-[2-(4-methoxy-7-morpholin-4-yl-benzothiazol-2-yl)-4,5,7,8-tetrahydro-1H-imidazo[4,5-d]azepin-6-yl]-methanone To a suspension of 0.04 g 2-(4-methoxy-7-morpholin-4-yl-benzothiazol-2-yl)-1,4,5,6,7,8-hexahydro-imidazo[4,5-d]azepine hydrochloride in 3.4 ml tetrahydrofurane were added at 0–4° C. 0.09 ml N-ethyldiisopropylamine and 0.017 g 2-chloromethyl-isonicotinoyl chloride hydrochloride. The mixture was refluxed for 17 hours, silicagel was added and the solvent was distilled off. The residue was transferred to a column prefilled with silicagel and was chromatographed with dichloromethane/methanol 96:4 to yield 0.037 g (68%) (2-chloromethyl-pyridin-4-yl)-[2-(4-methoxy-7-morpholin-4-yl-benzothiazol-2-yl)-4,5,7,8-tetrahydro-1H-imidazo[4,5-d]azepin-6-yl]-methanone as yellow solid; MS (ISP): m/e=540 (M+H$^+$).

EXAMPLE 42

[2-(4-Methoxy-7-morpholin-4-yl-benzothiazol-2-yl)-4,5,7,8-tetrahydro-1H-imidazo[4,5-d]azepin-6-yl]-(2-pyrrolidin-1-ylmethyl-pyridin-4-yl)-methanone A solution of 0.03 g (2-chloromethyl-pyridin-4-yl)-[2-(4-methoxy-7-morpholin-4-yl-benzothiazol-2-yl)-4,5,7,8-tetrahydro-1H-imidazo[4,5-d]azepin-6-yl]-methanone in 1 ml pyrrolidine was stirred at 40° C. for 18 hours. The pyrrolidine was distilled off and the residue was chromatographed with dichloromethane/methanol 95:5 to yield.0.018 g (61%) [2-(4-methoxy-7-morpholin-4-yl-benzothiazol-2-yl)-4,5,7,8-tetrahydro-1H-imidazo[4,5-d]azepin-6-yl]-(2-pyrrolidin-1-ylmethyl-pyridin-4-yl)-methanone as yellow solid; MS (ISP): m/e=574 (M+H$^+$).

EXAMPLE 43

[2-(4-Methoxy-7-morpholin-4-yl-benzothiazol-2-yl)-4,5,7,8-tetrahydro-1H-imidazo[4,5-d]azepin-6-yl]-(2-methyl-pyridin-4-yl)-methanone To a suspension of 0.04 g 2-(4-methoxy-7-morpholin-4-yl-benzothiazol-2-yl)-1,4,5,6,7,8-hexahydro-imidazo[4,5-d]azepine hydrochloride in 3.5 ml tetrahydrofurane were added at 0–4° C. 0.37 ml N-ethyldiisopropylamine and 0.19 mg 2-methyl-isonicotinoyl chloride hydrochloride. The mixture was refluxed for 17 hours, silicagel was added and the solvent was distilled off. The residue was transferred to a column prefilled with silicagel and was chromatographed with ethylacetate/methanol 9:1 to yield 0.025 g (50%) [2-(4-methoxy-7-morpholin-4-yl-benzothiazol-2-yl)-4,5,7,8-tetrahydro-1H-imidazo[4,5-d]azepin-6-yl]-(2-methyl-pyridin-4-yl)-methanone as yellow solid; MS (ISP): m/e=505 (M+H$^+$).

EXAMPLE 44

5-Benzyl-2-(4-methoxy-7-morpholin-4-yl-benzothiazol-2-yl)-4,5,6,7-tetrahydro-3H-imidazo[4,5-c]pyridine To a suspension of 0.04 g 4-methoxy-7-morpholin-4-yl-benzothiazole-2-carboximidothioic acid methyl ester hydroiodide in 1.8 ml tetrahydrofurane were added 0.1 g 1-benzyl-4,4-diethoxy-piperidin-3-ylamine in 1.8 ml tetrahydrofurane and the mixture was stirred at room temperature for 16 hours. Then 0.015 ml boron trifluoride etherate was added and the solvent was distilled off under vacuum. Again 0.015 ml boron trifluoride etherate was added and the mixture was dissolved in 1.5 ml dimethylformamide and heated for 15 minutes at 125° C. The solvent was distilled off and the residue was dissolved in dichloromethane and extracted with water. The organic layer was dried with sodium sulfate, filtered and the solvent was evaporated. Chromatography on silicagel with ethylacatate/heptane 1:1 to 2:1 yielded 0.4 mg (1%) 5-benzyl-2-(4-methoxy-7-morpholin-4-yl-benzothiazol-2-yl)-4,5,6,7-tetrahydro-3H-imidazo[4,5-c]pyridine as an amorphous solid; m/e=462 (M+H$^+$).

EXAMPLE 45

2-(1H-Imidazol-2-yl)-4-methoxy-7-(tetrahydro-pyran-4-yl)-benzothiazole 2.0 g Trifluoro-methanesulfonic acid 3,6-dihydro-2H-pyran-4-yl ester (8.6 mmol) and 2.89 g 2-(4-methoxy-3-nitro-phenyl)-4,4,5,5-tetramethyl-[1,3,2]dioxaborolane (10.3 mmol) were dissolved in a mixture of toluene (20 ml) and ethanol (50 ml) 0.35 g of dichloro (1,1'bis-(diphenylphosphine)ferrocene)palladium(II)dichloromethane (0.43 mmol) was added and heated to 85° C. Then aqueous sodium carbonate (2M) (10 ml) was added and the reaction kept at 85° C. for 45 min. After cooling to ambient temperature the reaction was extracted with ethyl acetate/water, the organic phase was dried over sodium sulfate and concentrated. Column chromatography on silica gel (n-heptane/ethyl acetate 4:1) yielded 1.33 g of 4-(4-methoxy-3-nitro-phenyl)-3,6-dihydro-2H-pyran (66%) as a yellow solid; M.p.: 117–120° C.

1.3 g 4-(4-Methoxy-3-nitro-phenyl)-3,6-dihydro-2H-pyran (5.5 mmol) was dissolved in ethanol (100 ml) and treated with Pd/C 10% (0.065 g) under an atmosphere of hydrogen for 16 h. After filtration, evaporation and drying of the residue, 0.82 g of 2-methoxy-5-(tetrahydro-pyran-4-yl)-phenylamine (71%) were obtained as an off-white solid; M.p.: 102–103° C.

To a suspension of 0.351 g of imidazole-2-carboxylic acid (3.13 mmol) in 15 ml DMF were added 0.508 g of CDI (3.13 mmol) and 0.43 ml triethylamine (3.13 mmol), and the mixture stirred at ambient temperature for 1 h. Then the mixture was refluxed for 30 min. After cooling to ambient temperature, 0.5 g of 2-methoxy-5-(tetrahydro-pyran-4-yl)-phenylamine (2.4 mmol) was added and the reaction mixture was heated to reflux for 16 h. The mixture was evaporated and the residue taken up in water (40 ml) and extracted 3 times with methylene chloride. The combined organic phases were tried on sodium carbonate, evaporated and the residue was stirred in hot ethyl acetate. After filtration and trying 0.42 g 1H-Imidazole-2-carboxylic acid [2-methoxy-5-(tetrahydro-pyran-4-yl)-phenyl]-amide (57%) were obtained as a yellow solid; M.p.: 227–228° C.

0.41 g of 1H-Imidazole-2-carboxylic acid [2-methoxy-5-(tetrahydro-pyran-4-yl)-phenyl]-amide (1.36 mmol) were taken up in toluene (25.0 ml) and treated with 1.65 g of Lawesson reagent (4.08 mmol). The reaction mixture was heated to reflux for 16 h. After cooling to ambient temperature, water (25 ml) was added and the mixture was extracted 3 times with methylene chloride. The combined organic phases were dried on sodium carbonate, evaporated and the residue was dried under high vacuum to yield 0.179 g of 1H-imidazole-2-carbothioic acid [2-methoxy-5-(tetrahydro-pyran-4-yl)-phenyl]-amide (41%) as a yellow solid; M.p.: 189–190° C.

0.085 g of 1H-Imidazole-2-carbothioic acid [2-methoxy-5-(tetrahydro-pyran-4-yl)-phenyl]-amide (0.27 mmol) was taken up in water (6.0 ml) and treated with 0.06 g KOH (1.07 mmol) and 0.331 g of potassium hexacyano ferrate (1.0 mmol) at reflux for 16 h. After cooling to ambient temperature water (10 ml) was added and the reaction mixture was extracted with methylene chloride and dried over sodium sulfate. The residue was dried in vacuo at 40° C. One obtained 0.035 g of 2-(1H-imidazol-2-yl)-4-methoxy-7-(tetrahydro-pyran-4-yl)-benzothiazole (41%) as a light brown solid; M.p.: 220–224° C.

EXAMPLE 46

2-[2-(4-Methoxy-7-morpholin-4-yl-benzothiazol-2-yl)-4,5,7,8-tetrahydro-1H-imidazo[4,5-d]azepin-6-yl]-acetamide To a suspension of 0.04 g 2-(4-methoxy-7-morpholin-4-yl-benzothiazol-2-yl)-1,4,5,6,7,8-hexahydro-imidazo[4,5-d]azepine hydrochloride in 5 ml acetonitrile were added 0.017 mg 2-bromoacetamide, 0.026 mg sodium carbonate and 0.018 mg sodium iodide. The mixture was refluxed for 17 hours, silicagel was added and the solvent was distilled off. The residue was transferred to a column prefilled with silicagel and was chromatographed with dichloromethane/methanol 95:5. Product containing fractions were further purified by chromatography on aluminium oxide with dichloromethane/methanol 95:5 to 4:1 to yield 0.015 g (34%) 2-[2-(4-methoxy-7-morpholin-4-yl-benzothiazol-2-yl)-4,5,7,8-tetrahydro-1H-imidazo[4,5-d]azepin-6-yl]-acetamide as yellow solid; M.p.: 299–302° C.; MS (ISP): m/e 443 (M+H⁺).

The invention claimed is:
1. A compound of formula Ia

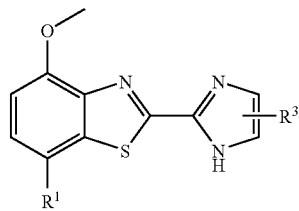

wherein
R¹ is selected from the group consisting of phenyl and a N- and O-containing heterocycle; and
R³ is selected from the group consisting of hydrogen, phenyl, 2,3-dihydro-benzo[1,4]dioxin-6-yl, benzo[b]thiophen-3-yl, 3-methyl-benzo[b]thiophen-2-yl, thiophen-2-yl, thiophen-3-yl and thiophen-2-yl-methyl;
or a pharmaceutically acceptable salt thereof.

2. A compound of formula Ib

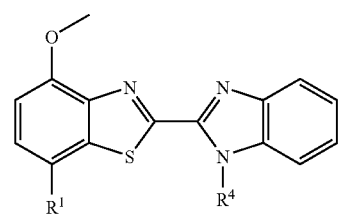

wherein
R¹ is a N- and/ O-containing heterocycle; and
R⁴ is selected from hydrogen and lower alkyl;
or a pharmaceutically acceptable salt thereof.

3. A compound of formula Id

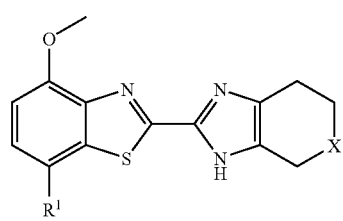

wherein
R¹ is a N- and O-containing heterocycle;
X CH₂; and
R'" is hydrogen;
or a pharmaceutically acceptable salt thereof.

4. The compound of formula Ia in accordance with claim 1, wherein R¹ is morpholinyl.

5. The compound of formula Ia in accordance with claim 1, which is selected from
2-(1H-imidazol-2-yl)-4-methoxy-7-morpholin-4-yl-benzothiazole,
2-(1H-imidazol-2-yl)-4-methoxy-7-phenyl-benzothiazole,
4-methoxy-7-morpholin-4-yl-2-(4-phenyl-1H-imidazol-2-yl)-benzothiazole,
2-[4-(2,3-dihydro-benzo[1,4]dioxin-6-yl)-1H-imidazol-2-yl]-4-methoxy-7-morpholin-4-yl-benzothiazole,
2-(5-benzo[b]thiophen-3-yl-1H-imidazol-2-yl)-4-methoxy-7-morpholin-4-yl-benzothiazole,
4-methoxy-7-morpholin-4-yl-2-(4-thiophen-2-yl-1H-imidazol-2-yl)-benzothiazole,
4-methoxy-7-morpholin-4-yl-2-(4-thiophen-3-yl-1H-imidazol-2-yl)-benzothiazole and
4-methoxy-7-morpholin-4-yl-2-(4-thiophen-2-ylmethyl-1H-imidazol-2-yl)-benzothiazole.

6. The compound of formula Ib in accordance with claim 2, which is selected from
2-(1H-benzoimidazol-2-yl)-4-methoxy-7-morpholin-4-yl-benzothiazole and 4-methoxy-2-(1-methyl-1H-benzoimidazol-2-yl)-7-morpholin-4-yl-benzothiazole.

7. The compound of formula Id in accordance with claim 3, which is
4-methoxy-7-morpholin-4-yl-2-(4,5,6,7-tetrahydro-1H-benzoimidazol-2-yl)-benzothiazole.

8. A process for preparing a compound of formula Ia as defined in claim 1, which process comprises reacting a compound of formula

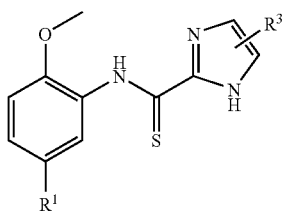

II with K$_3$FeCN$_6$/KOH
to produce a compound of formula

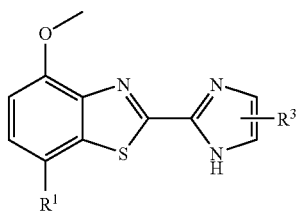

Ia wherein,
R$^1$ is selected from the group consisting of phenyl, N-containing heterocycle, O-containing heterocycle and both N- and O-containing heterocycle; and
R$^3$ is selected from the group consisting of hydrogen, phenyl, 2,3-dihydro-benzo[1,4]dioxin-6-yl, benzo[b]thiophen-3-yl,
3-methyl-benzo[b]thiophen-2-yl, thiophen-2-yl, thiophen-3-yl and thiophen-2-yl-methyl.

9. A process for preparing a compound of formula Ia1 as defined in claim 1, which process comprises cyclizing a compound of formula

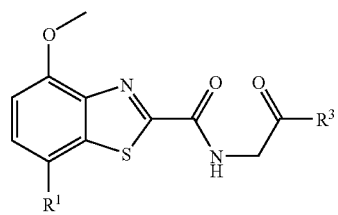

III to produce a compound of formula

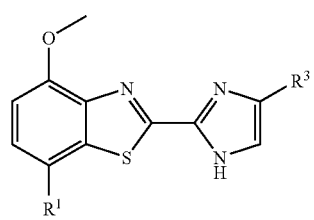

Ia1 wherein,
R$^1$ is selected from the group consisting of phenyl, N-containing heterocycle, O-containing heterocycle and both N- and O-containing heterocycle; and
R$^3$ is selected from the group consisting of hydrogen, phenyl, 2,3-dihydro-benzo[1,4]dioxin-6-yl, benzo[b]thiophen-3-yl,
3-methyl-benzo[b]thiophen-2-yl, thiophen-2-yl, thiophen-3-yl and thiophen-2-yl-methyl.

10. A process for preparing a compound of formula Ib as defined in claim 2, which process comprises reacting a compound of formula

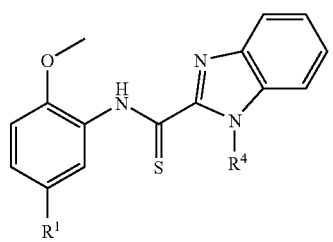

IV with K$_3$FeCN$_6$/KOH
to produce a compound of formula

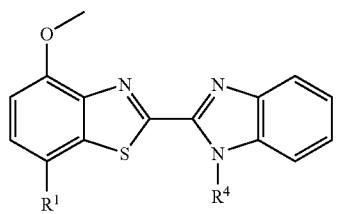

Ib wherein
R$^1$ is selected from the group consisting of phenyl, N-containing heterocycle, O-containing heterocycle and both N- and O-containing heterocycle; and
R$^4$ is selected from the group consisting of hydrogen and lower alkyl.

11. A process for preparing a compound of formula Ib as defined in claim 2, which process comprises methylating a compound of formula

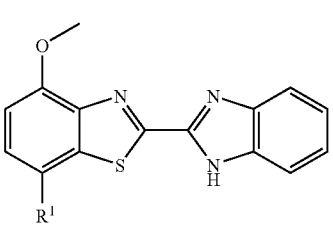

Ib2 to produce a compound of formula

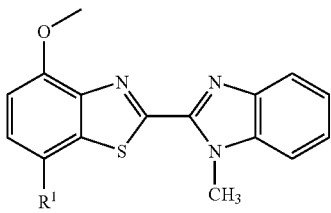
Ib1 wherein,
R¹ is selected from the group consisting of phenyl, N-containing heterocycle, O-containing heterocycle and both N- and O-containing heterocycle.

12. The process of claim 8, which further comprises converting the compounds obtained into a pharmaceutically acceptable salt.

13. The process of claim 9, which further comprises converting the compounds obtained into a pharmaceutically acceptable salt.

14. The process of claim 10, which further comprises converting the compounds obtained into a pharmaceutically acceptable salt.

15. The process of claim 11, which further comprises converting the compounds obtained into a pharmaceutically acceptable salt.

16. A pharmaceutical composition comprising a therapeutically effective amount of a compound of formula Ia

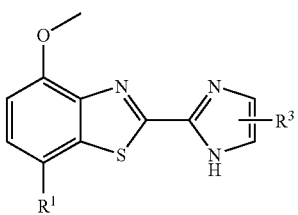
Ia wherein
R¹ is selected from the group consisting of phenyl and a N- and O-containing heterocycle; and
R³ is selected from the group consisting of hydrogen, phenyl, 2,3-dihydro-benzo[1,4]dioxin-6-yl, benzo[b]thiophen-3-yl, 3-methyl-benzol[b]thiophen-2-yl, thiophen-2-yl, thiophen-3-yl and thiophen-2-yl-methyl;
or a pharmaceutically acceptable salt thereof
and a pharmaceutically acceptable carrier.

17. A pharmaceutical composition comprising a therapeutically effective amount of a compound of formula Ib

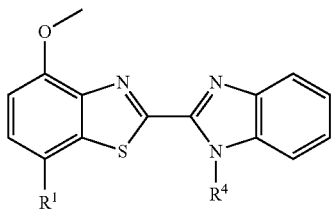
Ib wherein
R¹ is a N- and/ O-containing heterocycle; and
R⁴ is selected from hydrogen and lower alkyl;
or a pharmaceutically acceptable salt thereof
and a pharmaceutically acceptable carrier.

18. A pharmaceutical composition comprising a therapeutically effective amount of a compound of formula Id

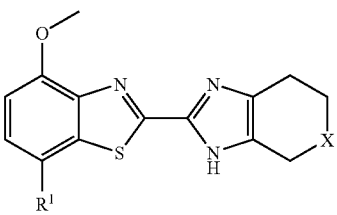
Id wherein
R¹ is a N- and O-containing heterocycle;
X is $CH_2$; and
R''' is hydrogen;
or a pharmaceutically acceptable salt thereof
and a pharmaceutically acceptable carrier.

19. The compound of formula Ib in accordance with claim 2, wherein R¹ is morpholinyl.

20. The compound of formula Id in accordance with claim 3, wherein R¹ is morpholinyl.

* * * * *

UNITED STATES PATENT AND TRADEMARK OFFICE
CERTIFICATE OF CORRECTION

| | |
|---|---|
| PATENT NO. | : 7,122,545 B2 |
| APPLICATION NO. | : 10/843241 |
| DATED | : October 17, 2006 |
| INVENTOR(S) | : Flohr et al. |

It is certified that error appears in the above-identified patent and that said Letters Patent is hereby corrected as shown below:

- Claim 3, Column 50, line 39: "X $CH_2$; and" should read -- X is $CH_2$ and --.

Signed and Sealed this

Seventh Day of August, 2007

JON W. DUDAS
*Director of the United States Patent and Trademark Office*